(12) United States Patent
Greider et al.

(10) Patent No.: US 11,156,599 B2
(45) Date of Patent: Oct. 26, 2021

(54) ASSAY FOR TELOMERE LENGTH REGULATORS

(71) Applicant: The Johns Hopkins University, Baltimore, MD (US)

(72) Inventors: Carol W. Greider, Baltimore, MD (US); Stella S. Lee, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 220 days.

(21) Appl. No.: 15/557,652

(22) PCT Filed: Mar. 18, 2016

(86) PCT No.: PCT/US2016/023114
§ 371 (c)(1),
(2) Date: Sep. 12, 2017

(87) PCT Pub. No.: WO2016/149612
PCT Pub. Date: Sep. 22, 2016

(65) Prior Publication Data
US 2018/0064746 A1 Mar. 8, 2018

Related U.S. Application Data

(60) Provisional application No. 62/184,148, filed on Jun. 24, 2015, provisional application No. 62/135,616, filed on Mar. 19, 2015.

(51) Int. Cl.
| | |
|---|---|
| *G01N 33/50* | (2006.01) |
| *C12N 15/86* | (2006.01) |
| *C12Q 1/6851* | (2018.01) |
| *C12Q 1/686* | (2018.01) |
| *C12N 15/113* | (2010.01) |
| *C12N 9/10* | (2006.01) |

(52) U.S. Cl.
CPC ....... *G01N 33/5008* (2013.01); *C12N 9/1077* (2013.01); *C12N 15/1137* (2013.01); *C12N 15/86* (2013.01); *C12Y 204/0203* (2013.01); *C12Y 207/11022* (2013.01); *C12N 2310/11* (2013.01); *C12N 2310/14* (2013.01); *C12N 2310/141* (2013.01); *C12N 2310/3231* (2013.01); *C12N 2310/531* (2013.01); *C12Q 1/686* (2013.01); *C12Q 1/6851* (2013.01)

(58) Field of Classification Search
CPC ...... C12Q 1/025; C12Q 1/686; C12Q 1/6851; C12N 15/907; G01N 33/5008; G01N 33/5011
See application file for complete search history.

(56) References Cited

U.S. PATENT DOCUMENTS

| | | | |
|---|---|---|---|
| 5,686,245 | A | 11/1997 | West et al. |
| 7,629,168 | B2 | 12/2009 | Tanaka et al. |
| 2004/0242461 | A1 | 12/2004 | Schneider |
| 2007/0086988 | A1 | 4/2007 | Tanaka et al. |
| 2014/0287946 | A1 | 9/2014 | Marble |

FOREIGN PATENT DOCUMENTS

| | | |
|---|---|---|
| WO | WO 2013/024264 A1 | 2/2013 |
| WO | WO 2014/138379 A1 | 9/2014 |

OTHER PUBLICATIONS

Kilburn et al. INsertion of a telomere repeat sequence into a mammalian gene causes chromosome instability. Molecular and Cellular Biology, vol. 21, No. 1, pp. 126-135, Jan. 2001. (Year: 2001).*
Ribeyre et al. Regulation of telomere addition at DNA double-strand breaks. Chromosoma, vol. 122, pp. 159-173, Mar. 7, 2013. (Year: 2013).*
Lee, SS., Bohrson, C., Pike, AM, Wheelan, SJ., and Greider, CW. ATM Kinase is Required for Telomere Elongation in Mouse and Human Cells. Cell Reports, vol. 13, No. 8, pp. 1623-1632, Epub Nov. 12, 2015, including pp. 1/15-15/15 of Supplemental Information. (Year: 2015).*
Reynolds et al. PIF1 disruption or NBS1 hypomorphism does not affect chromosome healing or fusion resulting from double-strand breaks near telomeres in murine embryonic stem cells. DNA Repair, vol. 10, pp. 1164-1173, Sep. 2011. (Year: 2011).*
Smith et al. Histone deacetylase inhibitors selectively target homology dependent DNA repair defective cells and elevate non-homologous endjoining activity. PLOS ONE, vol. 9, Issue 1, e87203, printed as pp. 1-12, Jan. 23, 2014. (Year: 2014).*
Wright et al. Aminoglycoside Phosphotransferases: Proteins, Structure, and Mechanism. Frontiers in Bioscience, vol. 4, pp. 9-21, Jan. 1999. (Year: 1999).*
Kipling, D. Telomere structure and telomerase expression during mouse development and tumorigenesis. European Journal of Cancer, vol. 33, pp. 792-800, Apr. 1997. (Year: 1997).*
Anglana and Bacchetti., "Construction of a Recombinant Adenovirus for Efficient Delivery of the I-ScelI Yeast Endonuclease to Human Cells and its Application in the in vivo Cleavage of Chromosomes to Expose New Potential Telomeres," *Nucleic Acids Res.* (1999), 27(21):4276-4281, Oxford University Press.
Bryant and Helleday, "Inhibition of Poly (ADP-Ribose) Polymerase Activates ATM which is Required for Subsequent Homologous Recombination Repair," *Nucleic Acids Res.* (2006), 34(6):1685-1691, Oxford University Press.
Frank et al., "Regulation of Telomere Elongation by the Cyclin-Dependent Kinase CDK1," *Mol. Cell* (2006), 24:423-432, Elsevier Inc.
Neumann et al., "Alternative Lengthening of Telomeres in Normal Mammalian Somatic Cells," *Genes Dev.* (2013), 27:18-23, Cold Spring Harbor Press.

\* cited by examiner

*Primary Examiner* — Jennifer Dunston
(74) *Attorney, Agent, or Firm* — Johns Hopkins Technology Ventures

(57) ABSTRACT

The present invention provides an assay that identifies genes required for telomerase-dependent telomere elongation by measuring the de novo telomere addition at a single chromosome.

9 Claims, 12 Drawing Sheets

Specification includes a Sequence Listing.

FIG. 3A

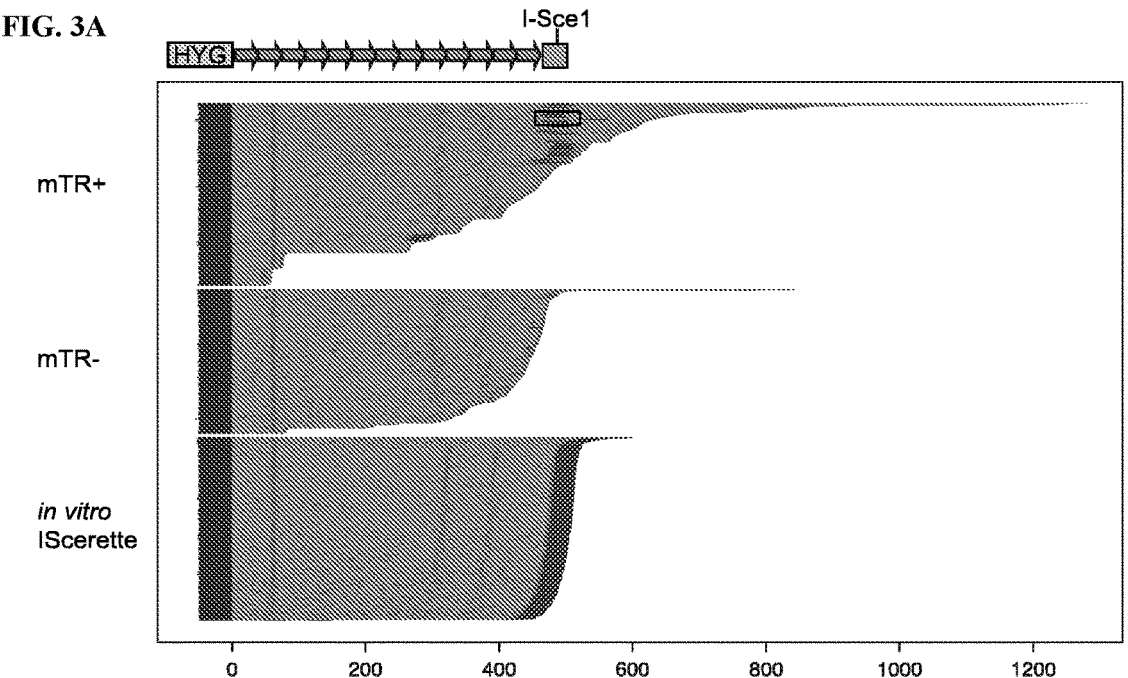

FIG. 3B

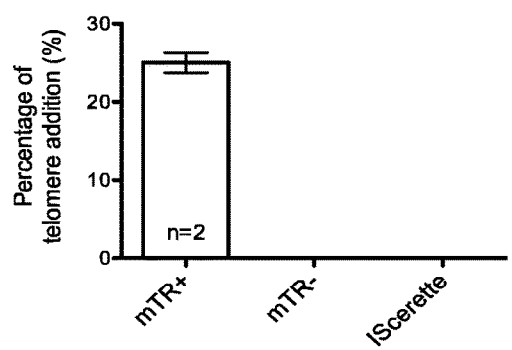

FIG. 3C

```
TAGGGTTAGGGTTAGGGTTAGGGTTAGGGAATTCCTGCAGCCCGGGGGATCCTAGGGTTAGGGTTAGGGTTA
GGTTAGGGTTAGGGTTAGGGTTAGGGAATTCCTGCAGCCCGGGGGATCCTAGGGTTAGGGTTAGGGTTAGGG
GGGTTAGGGGTTAGGGTTAGGGTTAGGGAATTCCTGCAGCCCGGGGGATCCTAGGGTTAGGGTTAGGGTTAG
AGGGTTAGGGTTAGGGTTAGGGAATTCCTGCAGCCCGGGGGATCCTAGGGTTAGGGTTAGGGTTAGGGTTAG
GGGTTAGGGTTAGGGTTAGGGTTAGGGAATTCCTGCAGCCCGGGGGATCCTAGGGTTAGGGTTAGGGTTAGG
GGGTTAGGGTTAGGGTTAGGGAATTCCTGCAGCCCGGGGGATCCTAGGGTTAGGGTTAGGGTTAGGGTTA
GTTAGGGTTAGGAATTCCTGCAGCCCGGGGGATCCTAGGGTTAGGGTTAGGGTTAGGGTTAGGGTTAGGGTT
TTAGGGTTAGGGTTAGGGTTAGGGTTAGGGAATTCCTGCAGCCCGGGCGGATCCTAGGGTTAGGGTTAGGGT
GGGTTAGGGTTAGGGTTAGGGAATTCCTGCAGCCCGGGGGATCCTAGGGTTAGGGTTAGGGTTAGGGTTAGG
GTTAGGGTTAGGGAATTCCTGCAGCCGGGGGATCCTAGGGTTAGGGTTAGGGTTAGGGTTAGGGTTAGGTAG
```

FIG. 5A
```
5'-GAATTCCTGCAGCCCGGGGGATCC TAGGGATAACAGGGTAAT     I-Sce1 recognition site
3'-CTTAAGGACGTCGGGCCCCCTAGG ATCCCTATTGTCCCATTA
                          ↓ I-Sce1 cleavage

5'-GAATTCCTGCAGCCCGGGGGATCCTAGGGATAA
3'-CTTAAGGACGTCGGGCCCCCTAGGATCCC

5'-TTAGGGTTAGGGTTAGGGTTAGGGTTAGGGTTAG              Telomere sequence
                        CUUUUAGUCCCAAUCCA-5'       mTR sequence
                        Primer-alignment Template
```

FIG. 5B

Class 1
n = 76 (11%)
```
5'-GAATTCCTGCAGCCCGGGGGATCCTAGGGATAA
                          CUUUUAGUCCCAAUCCA-5'
5'-GAATTCCTGCAGCCCGGGGGATCCTAGGGATAA GGGTTAGGGTTAGGG
```

Class 2
n = 62 (9%)
```
5'-GAATTCCTGCAGCCCGGGGGATCCTAGGGAT
                       CUUUUAGUCCCAAUCCA-5'
5'-GAATTCCTGCAGCCCGGGGGATCCTAGGGAT AGGGTTAGGGTTAGG
```

Class 3
n = 310 (44%)
```
5'-GAATTCCTGCAGCCCGGGGGATCCTAGGG
                     CUUUUAGUCCCAAUCCA-5'
5'-GAATTCCTGCAGCCCGGGGGATCCTAGGG TAGGGTTAGGG
```

Class 4
n = 62 (9%)
```
5'-GAATTCCTGCAGCCCGGGGGATC
                CUUUUAGUCCCAAUCCA-5'
5'-GAATTCCTGCAGCCCGGGGGATC GGGTTAGGGTTAGGG
```

Class 5
n = 168 (24%)
```
5'-GAATTCCTGCAGCCCGGGGG
            CUUUUAGUCCCAAUCCA-5'
5'-GAATTCCTGCAGCCCGGGGG TAGGGTTAGGG
```

Class 6
n = 19 (3%)
```
5'-GAATTCCTGCAG
       CUUUUAGUCCCAAUCCA-5'
5'-GAATTCCTGCAG GGTTAGGGTTAGG
```

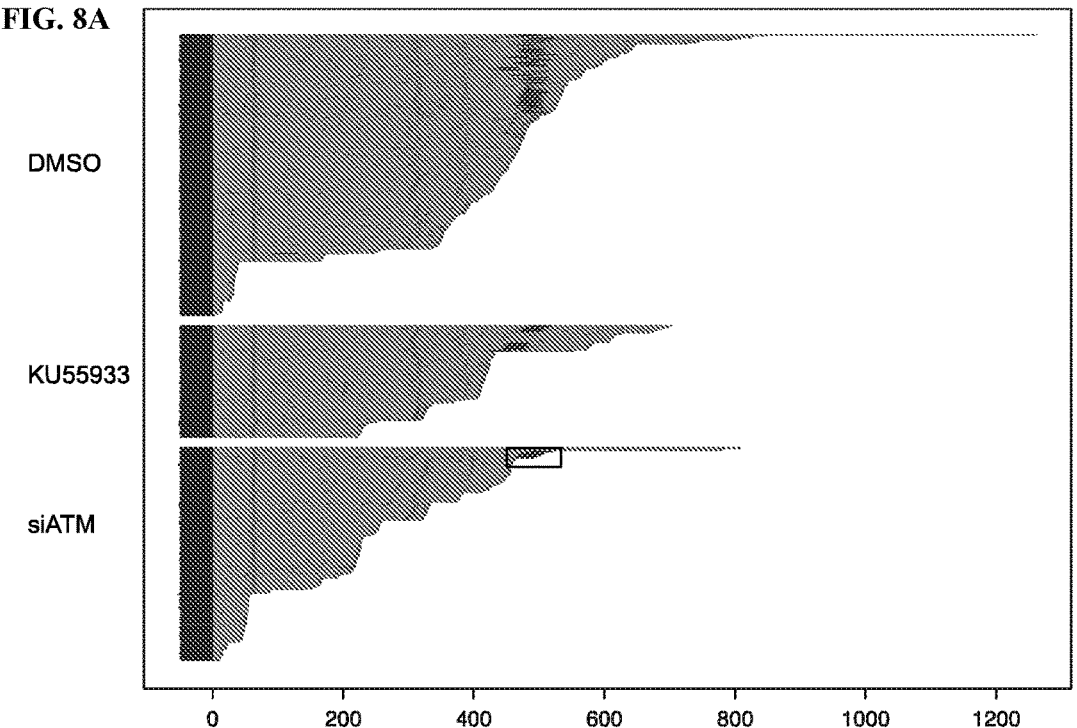
FIG. 8A
FIG. 8B
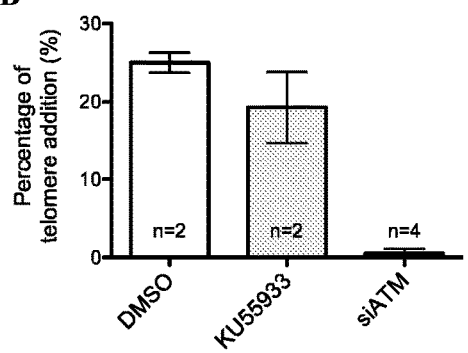
FIG. 8C

FIG. 10A
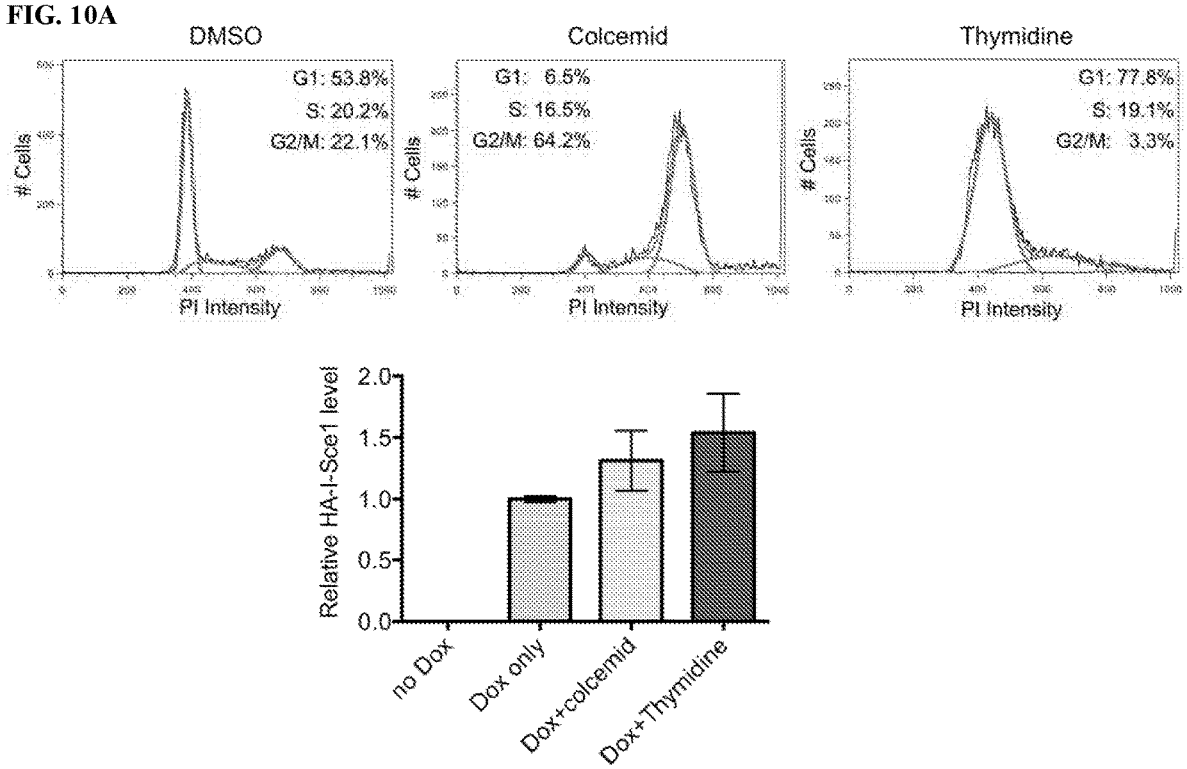
FIG. 10B
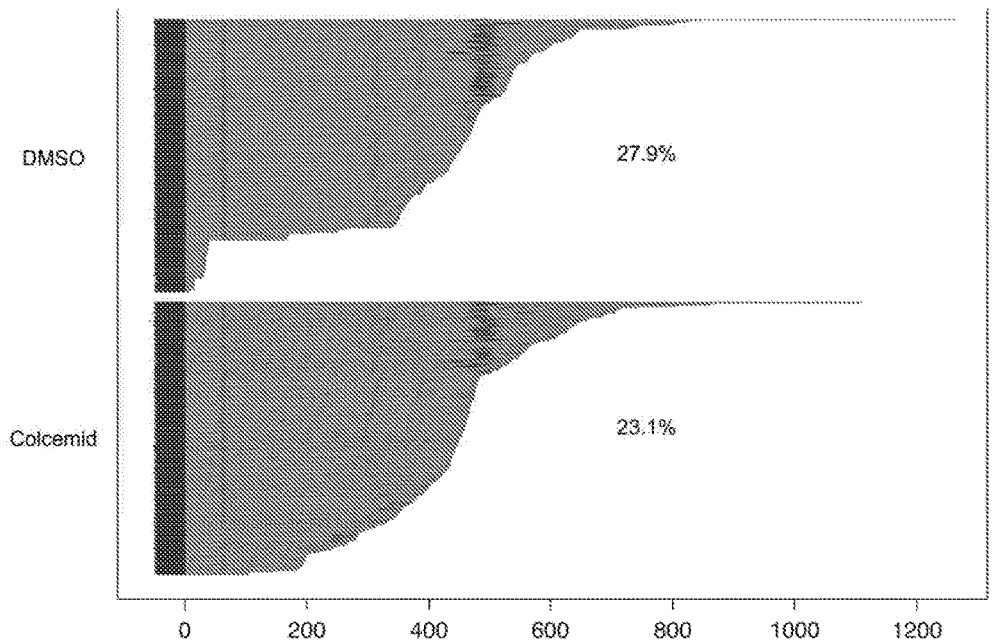
FIG. 10C

SEQUENCE LISTING

```
<160> NUMBER OF SEQ ID NOS: 146

<210> SEQ ID NO 1
<211> LENGTH: 72
<212> TYPE: DNA
<213> ORGANISM: Mus musculus

<400> SEQUENCE: 1
tagggttagg gttagggtta gggttaggga attcctgcag cccgggggat cctagggtta    60
gggttagggt ta                                                        72

<210> SEQ ID NO 2
<211> LENGTH: 72
<212> TYPE: DNA
<213> ORGANISM: Mus musculus

<400> SEQUENCE: 2
ggttagggtt sgggttaggg ttagggaatt cctgcagccc ggggatcct agggttaggg    60 ttagggttag gg                                                        72

<210> SEQ ID NO 3
<211> LENGTH: 72
<212> TYPE: DNA
<213> ORGANISM: Mus musculus

<400> SEQUENCE: 3
gggttagggg ttagggttag ggttagggaa ttcctgcagc ccgggggatc ctagggttag    60
ggttagggtt ag                                                        72

<210> SEQ ID NO 4
<211> LENGTH: 72
<212> TYPE: DNA
<213> ORGANISM: Mus musculus

<400> SEQUENCE: 4
agggttaggg ttagggttag ggaattcctg cagcccgggg gatcctaggg ttagggttag    60
ggttagggtt ag                                                        72

<210> SEQ ID NO 5
<211> LENGTH: 72
<212> TYPE: DNA
<213> ORGANISM: Mus musculus

<400> SEQUENCE: 5
```

```
gggttagggt tagggttagg gttagggaat tcctgcagcc cggggatcc tagggttagg      60 gttagggtta gg                                                          72

<210> SEQ ID NO 6
<211> LENGTH: 72
<212> TYPE: DNA
<213> ORGANISM: Mus musculus

<400> SEQUENCE: 6
gggttagggt tagggaattc ctgcagcccg ggatctagg ttaggttagg gttagggtta      60
gggttagggt ta                                                          72

<210> SEQ ID NO 7
<211> LENGTH: 72
<212> TYPE: DNA
<213> ORGANISM: Mus musculus

<400> SEQUENCE: 7
gttagggtta ggaattcctg cagcccgggg atcctaggg ttaggttag ggttagggtt      60 agggttaggg tt                                                          72

<210> SEQ ID NO 8
<211> LENGTH: 71
<212> TYPE: DNA
<213> ORGANISM: Mus musculus

<400> SEQUENCE: 8
ttaggttagg gttagggtta gggtagggga attcctgcag cccgggcgga tcctagggtt     60
agggttaggg t                                                           71

<210> SEQ ID NO 9
<211> LENGTH: 72
<212> TYPE: DNA
<213> ORGANISM: Mus musculus

<400> SEQUENCE: 9
gggttagggt tagggttagg gaattcctgc agcccggggg atcctagggt tagggttagg     60
gttagggtta gg                                                          72

<210> SEQ ID NO 10
<211> LENGTH: 72
<212> TYPE: DNA
<213> ORGANISM: Mus musculus

<400> SEQUENCE: 10
gttagggtta gggaattcct gcagccgggg gatcctaggg ttagggttag ggttaggtta     60
gggttaggtt ag                                                          72

<210> SEQ ID NO 11
<211> LENGTH: 42
<212> TYPE: DNA
<213> ORGANISM: Artificial Sequence
<220> FEATURE:
<223> OTHER INFORMATION: Synthetic

<400> SEQUENCE: 11
gaattcctgc agcccggggg atcctaggga ttaacgggta at                        42

<210> SEQ ID NO 12
<211> LENGTH: 42
```

```
<212> TYPE: DNA
<213> ORGANISM: Artificial Sequence
<220> FEATURE:
<223> OTHER INFORMATION: Synthetic

<400> SEQUENCE: 12
attaccctgt tatccctagg atcccccggg ctgcaggaat tc                         42

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
gaattcctgc acccggggga tcctagggat aa                                    32

<210> SEQ ID NO 14
<211> LENGTH: 29
<212> TYPE: DNA
<213> ORGANISM: Artificial Sequence
<220> FEATURE:
<223> OTHER INFORMATION: Synthetic

<400> SEQUENCE: 14
ccctaggatc ccccgggctg caggaattc                                        29

<210> SEQ ID NO 15
<211> LENGTH: 34
<212> TYPE: DNA
<213> ORGANISM: Artificial Sequence
<220> FEATURE:
<223> OTHER INFORMATION: Synthetic

<400> SEQUENCE: 15
ttagggttag ggttagggtt agggttaggg ttag                                  34

<210> SEQ ID NO 16
<211> LENGTH: 17
<212> TYPE: RNA
<213> ORGANISM: Artificial Sequence
<220> FEATURE:
<223> OTHER INFORMATION: Synthetic

<400> SEQUENCE: 16
accuaacccu gauuuuc                                                     17

<210> SEQ ID NO 17
<211> LENGTH: 33
<212> TYPE: DNA
<213> ORGANISM: Artificial Sequence
<220> FEATURE:
<223> OTHER INFORMATION: Synthetic

<400> SEQUENCE: 17
gaattcctgc agcccggggg atcctaggga taa                                   33

<210> SEQ ID NO 18
<211> LENGTH: 16
<212> TYPE: RNA
<213> ORGANISM: Artificial Sequence
<220> FEATURE:
<223> OTHER INFORMATION: Synthetic

<400> SEQUENCE: 18
```
accuaacccu gauuuc                                              16

<210> SEQ ID NO 19
<211> LENGTH: 48
<212> TYPE: DNA
<213> ORGANISM: Artificial Sequence
<220> FEATURE:
<223> OTHER INFORMATION: Synthetic

<400> SEQUENCE: 19
gaattcctgc agcccggggg atcctaggga taagggttag ggttaggg           48

<210> SEQ ID NO 20
<211> LENGTH: 31
<212> TYPE: DNA
<213> ORGANISM: Artificial Sequence
<220> FEATURE:
<223> OTHER INFORMATION: Synthetic

<400> SEQUENCE: 20
gaattcctgc agcccggggg atcctaggga t                             31

<210> SEQ ID NO 21
<211> LENGTH: 16
<212> TYPE: RNA
<213> ORGANISM: Artificial Sequence
<220> FEATURE:
<223> OTHER INFORMATION: Synthetic

<400> SEQUENCE: 21
accuaaccug auuuuc                                              16

<210> SEQ ID NO 22
<211> LENGTH: 48
<212> TYPE: DNA
<213> ORGANISM: Artificial Sequence
<220> FEATURE:
<223> OTHER INFORMATION: Synthetic

<400> SEQUENCE: 22
gaattcctgc agcccggggg atcctaggga tcagggttag ggttaggg           48

<210> SEQ ID NO 23
<211> LENGTH: 29
<212> TYPE: DNA
<213> ORGANISM: Artificial Sequence
<220> FEATURE:
<223> OTHER INFORMATION: Synthetic

<400> SEQUENCE: 23
gaattcctgc agcccggggg atcctaggg                                29

<210> SEQ ID NO 24
<211> LENGTH: 17
<212> TYPE: RNA
<213> ORGANISM: Artificial Sequence
<220> FEATURE:
<223> OTHER INFORMATION: Synthetic

<400> SEQUENCE: 24
accuaacccu gauuuuc                                             17

<210> SEQ ID NO 25
<211> LENGTH: 41
<212> TYPE: DNA
<213> ORGANISM: Artificial Sequence -continued
<220> FEATURE:
<223> OTHER INFORMATION: Synthetic

<400> SEQUENCE: 25
gaattcctgc agcccggggg atcctagggt tagggttagg g           41

<210> SEQ ID NO 26
<211> LENGTH: 23
<212> TYPE: DNA
<213> ORGANISM: Artificial Sequence
<220> FEATURE:
<223> OTHER INFORMATION: Synthetic

<400> SEQUENCE: 26
gaattcctgc agcccggggg atc                              23

<210> SEQ ID NO 27
<211> LENGTH: 17
<212> TYPE: RNA
<213> ORGANISM: Artificial Sequence
<220> FEATURE:
<223> OTHER INFORMATION: Synthetic

<400> SEQUENCE: 27
accuaacccu gauuuuc                                     17

<210> SEQ ID NO 28
<211> LENGTH: 39
<212> TYPE: DNA
<213> ORGANISM: Artificial Sequence
<220> FEATURE:
<223> OTHER INFORMATION: Synthetic

<400> SEQUENCE: 28
gaattcctgc agcccggggg atcagggtta gggttaggg             39

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gaattcctgc agcccggggg                                  20

<210> SEQ ID NO 30
<211> LENGTH: 17
<212> TYPE: RNA
<213> ORGANISM: Artificial Sequence
<220> FEATURE:
<223> OTHER INFORMATION: Synthetic

<400> SEQUENCE: 30
accuaacccu gauuuuc                                     17

<210> SEQ ID NO 31
<211> LENGTH: 32
<212> TYPE: DNA
<213> ORGANISM: Artificial Sequence
<220> FEATURE:
<223> OTHER INFORMATION: Synthetic

<400> SEQUENCE: 31
gaattcctgc agcccggggg ttagggttag gg                    32

-continued

<210> SEQ ID NO 32
<211> LENGTH: 12
<212> TYPE: DNA
<213> ORGANISM: Artificial Sequence
<220> FEATURE:
<223> OTHER INFORMATION: Synthetic

<400> SEQUENCE: 32
gaattcctgc ag                                                          12

<210> SEQ ID NO 33
<211> LENGTH: 17
<212> TYPE: RNA
<213> ORGANISM: Artificial Sequence
<220> FEATURE:
<223> OTHER INFORMATION: Synthetic

<400> SEQUENCE: 33
accuaacccu gauuuuc                                                     17

<210> SEQ ID NO 34
<211> LENGTH: 26
<212> TYPE: DNA
<213> ORGANISM: Artificial Sequence
<220> FEATURE:
<223> OTHER INFORMATION: Synthetic

<400> SEQUENCE: 34
gaattcctgc agggttaggg ttaggg                                           26

<210> SEQ ID NO 35
<211> LENGTH: 82
<212> TYPE: DNA
<213> ORGANISM: Mus musculus

<400> SEQUENCE: 35
gggttagggt tagggttagg gttaggttag ggttaagggt tagggttagg gttagggtta      60
gggttagggt tagggggttag gg                                              82

<210> SEQ ID NO 36
<211> LENGTH: 74
<212> TYPE: DNA
<213> ORGANISM: Mus musculus

<400> SEQUENCE: 36
gttagggtag ggttagggtt agggttaggg ttagggttag gttagggtta gggttagggt      60
tagggttagg gtta                                                        74

<210> SEQ ID NO 37
<211> LENGTH: 46
<212> TYPE: DNA
<213> ORGANISM: Mus musculus

<400> SEQUENCE: 37
gggttagggt ttagggaatt cctgcagccc ggggatctt agggtg                      46

<210> SEQ ID NO 38
<211> LENGTH: 67
<212> TYPE: DNA
<213> ORGANISM: Mus musculus

<400> SEQUENCE: 38
ttagggttag gggttagggt tagggttagg gaattcctgg caggcccggg ggatccctag      60

```
                                    -continued gggttag                                                               67

<210> SEQ ID NO 39
<211> LENGTH: 57
<212> TYPE: DNA
<213> ORGANISM: Mus musculus

<400> SEQUENCE: 39
gttagggtta gggttagggt tagggaattc ctgcagcccg gggatccta gggttag        57

<210> SEQ ID NO 40
<211> LENGTH: 54
<212> TYPE: DNA
<213> ORGANISM: Mus musculus

<400> SEQUENCE: 40
tagggttagg gttagggtta gggaattcct gcagcccggg ggatcctagg gttg           54

<210> SEQ ID NO 41
<211> LENGTH: 48
<212> TYPE: DNA
<213> ORGANISM: Mus musculus

<400> SEQUENCE: 41
ttagggttag ggttagggaa ttcctgcagc ccgggggatc ctagggtg                  48

<210> SEQ ID NO 42
<211> LENGTH: 50
<212> TYPE: DNA
<213> ORGANISM: Mus musculus

<400> SEQUENCE: 42
ttagggttag ggttagggaa ttcctgcagc ccgggggatc ctagggttag                50

<210> SEQ ID NO 43
<211> LENGTH: 11
<212> TYPE: DNA
<213> ORGANISM: Mus musculus

<400> SEQUENCE: 43
tagggttagg g                                                          11

<210> SEQ ID NO 44
<211> LENGTH: 10
<212> TYPE: DNA
<213> ORGANISM: Mus musculus

<400> SEQUENCE: 44
tagggttagg                                                            10

<210> SEQ ID NO 45
<211> LENGTH: 51
<212> TYPE: DNA
<213> ORGANISM: Mus musculus

<400> SEQUENCE: 45
tagggttagg agggttagga attcctgcag cccggggatc ctagggttag g              51

<210> SEQ ID NO 46
<211> LENGTH: 10
<212> TYPE: DNA
<213> ORGANISM: Mus musculus
<220> FEATURE:
```

-continued

```
<221> NAME/KEY: misc_feature
<222> LOCATION: (1)..(2)
<223> OTHER INFORMATION: n is a, c, g, or t

<400> SEQUENCE: 46 nnggttaggg                                                                10

<210> SEQ ID NO 47
<211> LENGTH: 10
<212> TYPE: DNA
<213> ORGANISM: Mus musculus
<220> FEATURE:
<221> NAME/KEY: misc_feature
<222> LOCATION: (1)..(4)
<223> OTHER INFORMATION: n is a, c, g, or t

<400> SEQUENCE: 47 nnnngttagg                                                                10

<210> SEQ ID NO 48
<211> LENGTH: 10
<212> TYPE: DNA
<213> ORGANISM: Mus musculus
<220> FEATURE:
<221> NAME/KEY: misc_feature
<222> LOCATION: (1)..(4)
<223> OTHER INFORMATION: n is a, c, g, or t

<400> SEQUENCE: 48 nnnnttaggg                                                                10

<210> SEQ ID NO 49
<211> LENGTH: 10
<212> TYPE: DNA
<213> ORGANISM: Mus musculus
<220> FEATURE:
<221> NAME/KEY: misc_feature
<222> LOCATION: (1)..(4)
<223> OTHER INFORMATION: n is a, c, g, or t

<400> SEQUENCE: 49 nnnnggttag                                                                10

<210> SEQ ID NO 50
<211> LENGTH: 37
<212> TYPE: DNA
<213> ORGANISM: Mus musculus

<400> SEQUENCE: 50
tagggaattc ctgcagcccg ggggatccta gggttag                                  37

<210> SEQ ID NO 51
<211> LENGTH: 10
<212> TYPE: DNA
<213> ORGANISM: Mus musculus
<220> FEATURE:
<221> NAME/KEY: misc_feature
<222> LOCATION: (1)..(5)
<223> OTHER INFORMATION: n is a, c, g, or t

<400> SEQUENCE: 51 nnnnntaggg                                                                10

<210> SEQ ID NO 52
<211> LENGTH: 21
<212> TYPE: DNA
<213> ORGANISM: Artificial Sequence
```

<220> FEATURE:
<223> OTHER INFORMATION: Synthetic

<400> SEQUENCE: 52
ggcctcgaga tatcttctgc t                                    21

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
gccgttaaca gaggaaccaa g                                    21

<210> SEQ ID NO 54
<211> LENGTH: 25
<212> TYPE: DNA
<213> ORGANISM: Artificial Sequence
<220> FEATURE:
<223> OTHER INFORMATION: Synthetic

<400> SEQUENCE: 54
atacgactca ctatagggcg aattg                                25

<210> SEQ ID NO 55
<211> LENGTH: 24
<212> TYPE: DNA
<213> ORGANISM: Artificial Sequence
<220> FEATURE:
<223> OTHER INFORMATION: Synthetic

<400> SEQUENCE: 55
gtccagcata aaggcaaatg tggc                                 24

<210> SEQ ID NO 56
<211> LENGTH: 36
<212> TYPE: DNA
<213> ORGANISM: Artificial Sequence
<220> FEATURE:
<223> OTHER INFORMATION: Synthetic

<400> SEQUENCE: 56
gccgcgtcga cattaaccct cactaaaggg aacaaa                    36

<210> SEQ ID NO 57
<211> LENGTH: 25
<212> TYPE: DNA
<213> ORGANISM: Artificial Sequence
<220> FEATURE:
<223> OTHER INFORMATION: Synthetic

<400> SEQUENCE: 57
atacgactca ctatagggcg aattg                                25

<210> SEQ ID NO 58
<211> LENGTH: 48
<212> TYPE: DNA
<213> ORGANISM: Artificial Sequence
<220> FEATURE:
<223> OTHER INFORMATION: Synthetic

<400> SEQUENCE: 58
ggcttaatta atagaggatc gatcttggtg gcgtgaaact cccgcacc       48

<210> SEQ ID NO 59
<211> LENGTH: 47
<212> TYPE: DNA
<213> ORGANISM: Artificial Sequence
<220> FEATURE:
<223> OTHER INFORMATION: Synthetic

<400> SEQUENCE: 59
ctggcggccg ctcccgcgga aactcggccg tggtgaccaa tacaaaa        47

<210> SEQ ID NO 60
<211> LENGTH: 67
<212> TYPE: DNA
<213> ORGANISM: Artificial Sequence
<220> FEATURE:
<223> OTHER INFORMATION: Synthetic

<400> SEQUENCE: 60
gccgttaacg aagttcctat tctctagaaa gtataggaac ttcgcgcctg ccttctgtca        60
aattctg        67

<210> SEQ ID NO 61
<211> LENGTH: 33
<212> TYPE: DNA
<213> ORGANISM: Artificial Sequence
<220> FEATURE:
<223> OTHER INFORMATION: Synthetic

<400> SEQUENCE: 61
gccgaattcc ggatctacgc ctgtagtcct ccc        33

<210> SEQ ID NO 62
<211> LENGTH: 34
<212> TYPE: DNA
<213> ORGANISM: Artificial Sequence
<220> FEATURE:
<223> OTHER INFORMATION: Synthetic

<400> SEQUENCE: 62
gggcccgcga attctcgtaa tagtaatcaa ttac        34

<210> SEQ ID NO 63
<211> LENGTH: 34
<212> TYPE: DNA
<213> ORGANISM: Artificial Sequence
<220> FEATURE:
<223> OTHER INFORMATION: Synthetic

<400> SEQUENCE: 63
cgccccatcg atgaagttcc tatactttct agag        34

<210> SEQ ID NO 64
<211> LENGTH: 51
<212> TYPE: DNA
<213> ORGANISM: Artificial Sequence
<220> FEATURE:
<223> OTHER INFORMATION: Synthetic

<400> SEQUENCE: 64
caaattacaa aaattcaaaa ttttatcgat atccgccgcc actatgggat c        51

<210> SEQ ID NO 65
<211> LENGTH: 43
<212> TYPE: DNA
<213> ORGANISM: Artificial Sequence

```
<220> FEATURE:
<223> OTHER INFORMATION: Synthetic

<400> SEQUENCE: 65
ggaactccca agcttatcga ttcgatcgac ttattatttc agg                    43

<210> SEQ ID NO 66
<211> LENGTH: 43
<212> TYPE: DNA
<213> ORGANISM: Artificial Sequence
<220> FEATURE:
<223> OTHER INFORMATION: Synthetic

<400> SEQUENCE: 66
cctgaaataa taagtcgatc gaatcgataa gcttgggagt tcc                    43

<210> SEQ ID NO 67
<211> LENGTH: 43
<212> TYPE: DNA
<213> ORGANISM: Artificial Sequence
<220> FEATURE:
<223> OTHER INFORMATION: Synthetic

<400> SEQUENCE: 67
gacgttctca gtgctatcca tggttgtggc catattatca tcg                    43

<210> SEQ ID NO 68
<211> LENGTH: 43
<212> TYPE: DNA
<213> ORGANISM: Artificial Sequence
<220> FEATURE:
<223> OTHER INFORMATION: Synthetic

<400> SEQUENCE: 68
cgatgataat atggccacaa ccatggatag cactgagaac gtc                    43

<210> SEQ ID NO 69
<211> LENGTH: 37
<212> TYPE: DNA
<213> ORGANISM: Artificial Sequence
<220> FEATURE:
<223> OTHER INFORMATION: Synthetic

<400> SEQUENCE: 69
cgacgcggcc gctttacttc tactggaaca ggtggtg                           37

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
tgatcagtca acggggaca                                               20

<210> SEQ ID NO 71
<211> LENGTH: 21
<212> TYPE: DNA
<213> ORGANISM: Artificial Sequence
<220> FEATURE:
<223> OTHER INFORMATION: Synthetic

<400> SEQUENCE: 71
ttcgagaggt cctttcacc a                                             21
```

<210> SEQ ID NO 72
<211> LENGTH: 26
<212> TYPE: DNA
<213> ORGANISM: Artificial Sequence
<220> FEATURE:
<223> OTHER INFORMATION: Synthetic

<400> SEQUENCE: 72
tgtgggttct ggtcttttgt tctccg                                            26

<210> SEQ ID NO 73
<211> LENGTH: 22
<212> TYPE: DNA
<213> ORGANISM: Artificial Sequence
<220> FEATURE:
<223> OTHER INFORMATION: Synthetic

<400> SEQUENCE: 73 gttttttgagg ctcgggaacg cg                                               22

<210> SEQ ID NO 74
<211> LENGTH: 18
<212> TYPE: DNA
<213> ORGANISM: Artificial Sequence
<220> FEATURE:
<223> OTHER INFORMATION: Synthetic

<400> SEQUENCE: 74
aatccgtcga gcagagtt                                                     18

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
cccttaccct tacccttacc ctta                                              24

<210> SEQ ID NO 76
<211> LENGTH: 18
<212> TYPE: DNA
<213> ORGANISM: Artificial Sequence
<220> FEATURE:
<223> OTHER INFORMATION: Synthetic

<400> SEQUENCE: 76
atcgcttctc ggccttt                                                      18

<210> SEQ ID NO 77
<211> LENGTH: 36
<212> TYPE: DNA
<213> ORGANISM: Artificial Sequence
<220> FEATURE:
<223> OTHER INFORMATION: Synthetic

<400> SEQUENCE: 77
aatccgtcga gcagagttaa aaggccgaga agcgat                                 36

<210> SEQ ID NO 78
<211> LENGTH: 30
<212> TYPE: DNA
<213> ORGANISM: Artificial Sequence
<220> FEATURE:
<223> OTHER INFORMATION: Synthetic

```
<400> SEQUENCE: 78
atgaaaaagc ctgaactcac cgcgacgtct                                          30

<210> SEQ ID NO 79
<211> LENGTH: 24
<212> TYPE: DNA
<213> ORGANISM: Artificial Sequence
<220> FEATURE:
<223> OTHER INFORMATION: Synthetic

<400> SEQUENCE: 79
gtgctggggc gtcggtttcc acta                                                24

<210> SEQ ID NO 80
<211> LENGTH: 27
<212> TYPE: DNA
<213> ORGANISM: Artificial Sequence
<220> FEATURE:
<223> OTHER INFORMATION: Synthetic

<400> SEQUENCE: 80
tgctccgtgc atctggcatc ccctaac                                             27

<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81
tgctccgtgc atctggcatc taaccct                                             27

<210> SEQ ID NO 82
<211> LENGTH: 27
<212> TYPE: DNA
<213> ORGANISM: Artificial Sequence
<220> FEATURE:
<223> OTHER INFORMATION: Synthetic

<400> SEQUENCE: 82
tgctccgtgc atctggcatc cctaacc                                             27

<210> SEQ ID NO 83
<211> LENGTH: 27
<212> TYPE: DNA
<213> ORGANISM: Artificial Sequence
<220> FEATURE:
<223> OTHER INFORMATION: Synthetic

<400> SEQUENCE: 83
tgctccgtgc atctggcatc ctaaccc                                             27

<210> SEQ ID NO 84
<211> LENGTH: 27
<212> TYPE: DNA
<213> ORGANISM: Artificial Sequence
<220> FEATURE:
<223> OTHER INFORMATION: Synthetic

<400> SEQUENCE: 84
tgctccgtgc atctggcatc aacccta                                             27

<210> SEQ ID NO 85
```

```
<210> SEQ ID NO 85
<211> LENGTH: 27
<212> TYPE: DNA
<213> ORGANISM: Artificial Sequence
<220> FEATURE:
<223> OTHER INFORMATION: Synthetic

<400> SEQUENCE: 85
tgctccgtgc atctggcatc accctaa                                    27

<210> SEQ ID NO 86
<211> LENGTH: 24
<212> TYPE: DNA
<213> ORGANISM: Artificial Sequence
<220> FEATURE:
<223> OTHER INFORMATION: Synthetic

<400> SEQUENCE: 86
tgctccgtgc atctggcatc ttat                                       24

<210> SEQ ID NO 87
<211> LENGTH: 22
<212> TYPE: DNA
<213> ORGANISM: Artificial Sequence
<220> FEATURE:
<223> OTHER INFORMATION: Synthetic

<400> SEQUENCE: 87
ctgaactcac cgcgacgtct gt                                         22

<210> SEQ ID NO 88
<211> LENGTH: 25
<212> TYPE: DNA
<213> ORGANISM: Artificial Sequence
<220> FEATURE:
<223> OTHER INFORMATION: Synthetic

<400> SEQUENCE: 88
aggagggcgt ggatatgtcc tgcgg                                      25

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
tgctccgtgc atctggcatc                                            20

<210> SEQ ID NO 90
<211> LENGTH: 27
<212> TYPE: DNA
<213> ORGANISM: Artificial Sequence
<220> FEATURE:
<223> OTHER INFORMATION: Synthetic

<400> SEQUENCE: 90
tgctccgtgc atctggcatc ccctaac                                    27

<210> SEQ ID NO 91
<211> LENGTH: 27
<212> TYPE: DNA
<213> ORGANISM: Artificial Sequence
<220> FEATURE:
<223> OTHER INFORMATION: Synthetic

<400> SEQUENCE: 91
```
tgctccgtgc atctggcatc taacccc                                                27

<210> SEQ ID NO 92
<211> LENGTH: 27
<212> TYPE: DNA
<213> ORGANISM: Artificial Sequence
<220> FEATURE:
<223> OTHER INFORMATION: Synthetic

<400> SEQUENCE: 92
tgctccgtgc atctggcatc cctaacc                                                27

<210> SEQ ID NO 93
<211> LENGTH: 27
<212> TYPE: DNA
<213> ORGANISM: Artificial Sequence
<220> FEATURE:
<223> OTHER INFORMATION: Synthetic

<400> SEQUENCE: 93
tgctccgtgc atctggcatc ctaaccc                                                27

<210> SEQ ID NO 94
<211> LENGTH: 27
<212> TYPE: DNA
<213> ORGANISM: Artificial Sequence
<220> FEATURE:
<223> OTHER INFORMATION: Synthetic

<400> SEQUENCE: 94
tgctccgtgc atctggcatc aacccta                                                27

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
tgctccgtgc atctggcatc accctaa                                                27

<210> SEQ ID NO 96
<211> LENGTH: 24
<212> TYPE: DNA
<213> ORGANISM: Artificial Sequence
<220> FEATURE:
<223> OTHER INFORMATION: Synthetic

<400> SEQUENCE: 96
tgctccgtgc atctggcatc ttat                                                   24

<210> SEQ ID NO 97
<211> LENGTH: 22
<212> TYPE: DNA
<213> ORGANISM: Artificial Sequence
<220> FEATURE:
<223> OTHER INFORMATION: Synthetic

<400> SEQUENCE: 97
ctgaactcac cgcgacgtct gt                                                     22

<210> SEQ ID NO 98
<211> LENGTH: 25
<212> TYPE: DNA

```
<213> ORGANISM: Artificial Sequence
<220> FEATURE:
<223> OTHER INFORMATION: Synthetic

<400> SEQUENCE: 98
aggagggcgt ggatatgtcc tgcgg                                              25

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
tgctccgtgc atctggcatc                                                   20

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
tgctcgcgta cctgtgcatc                                                   20

<210> SEQ ID NO 101
<211> LENGTH: 27
<212> TYPE: DNA
<213> ORGANISM: Artificial Sequence
<220> FEATURE:
<223> OTHER INFORMATION: Synthetic

<400> SEQUENCE: 101
tgctcgcgta cctgtgcatc ccctaac                                           27

<210> SEQ ID NO 102
<211> LENGTH: 27
<212> TYPE: DNA
<213> ORGANISM: Artificial Sequence
<220> FEATURE:
<223> OTHER INFORMATION: Synthetic

<400> SEQUENCE: 102
tgctcgcgta cctgtgcatc taaccct                                           27

<210> SEQ ID NO 103
<211> LENGTH: 27
<212> TYPE: DNA
<213> ORGANISM: Artificial Sequence
<220> FEATURE:
<223> OTHER INFORMATION: Synthetic

<400> SEQUENCE: 103
tgctcgcgta cctgtgcatc cctaacc                                           27

<210> SEQ ID NO 104
<211> LENGTH: 27
<212> TYPE: DNA
<213> ORGANISM: Artificial Sequence
<220> FEATURE:
<223> OTHER INFORMATION: Synthetic

<400> SEQUENCE: 104
tgctcgcgta cctgtgcatc ctaaccc                                           27
```

<210> SEQ ID NO 105
<211> LENGTH: 27
<212> TYPE: DNA
<213> ORGANISM: Artificial Sequence
<220> FEATURE:
<223> OTHER INFORMATION: Unknown

<400> SEQUENCE: 105
tgctcgcgta cctgtgcatc aaccta                                27

<210> SEQ ID NO 106
<211> LENGTH: 27
<212> TYPE: DNA
<213> ORGANISM: Artificial Sequence
<220> FEATURE:
<223> OTHER INFORMATION: Synthetic

<400> SEQUENCE: 106
tgctcgcgta cctgtgcatc accctaa                               27

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
tgcgcactgc atgtgtcctc                                       20

<210> SEQ ID NO 108
<211> LENGTH: 27
<212> TYPE: DNA
<213> ORGANISM: Artificial Sequence
<220> FEATURE:
<223> OTHER INFORMATION: Synthetic

<400> SEQUENCE: 108
tgcgcactgc atgtgtcctc ccctaac                               27

<210> SEQ ID NO 109
<211> LENGTH: 27
<212> TYPE: DNA
<213> ORGANISM: Artificial Sequence
<220> FEATURE:
<223> OTHER INFORMATION: Synthetic

<400> SEQUENCE: 109
tgcgcactgc atgtgtcctc taaccct                               27

<210> SEQ ID NO 110
<211> LENGTH: 27
<212> TYPE: DNA
<213> ORGANISM: Artificial Sequence
<220> FEATURE:
<223> OTHER INFORMATION: Synthetic

<400> SEQUENCE: 110
tgcgcactgc atgtgtcctc cctaacc                               27

<210> SEQ ID NO 111
<211> LENGTH: 27
<212> TYPE: DNA
<213> ORGANISM: Artificial Sequence
<220> FEATURE:

<223> OTHER INFORMATION: Synthetic

<400> SEQUENCE: 111
tgcgcactgc atgtgtcctc ctaaccc                               27

<210> SEQ ID NO 112
<211> LENGTH: 27
<212> TYPE: DNA
<213> ORGANISM: Artificial Sequence
<220> FEATURE:
<223> OTHER INFORMATION: Synthetic

<400> SEQUENCE: 112
tgcgcactgc atgtgtcctc aacccta                               27

<210> SEQ ID NO 113
<211> LENGTH: 27
<212> TYPE: DNA
<213> ORGANISM: Artificial Sequence
<220> FEATURE:
<223> OTHER INFORMATION: Synthetic

<400> SEQUENCE: 113
tgcgcactgc atgtgtcctc accctaa                               27

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
tgcgtgtccc tgcatgcatc                                       20

<210> SEQ ID NO 115
<211> LENGTH: 27
<212> TYPE: DNA
<213> ORGANISM: Artificial Sequence
<220> FEATURE:
<223> OTHER INFORMATION: Synthetic

<400> SEQUENCE: 115
tgcgtgtccc tgcatgcatc ccctaac                               27

<210> SEQ ID NO 116
<211> LENGTH: 27
<212> TYPE: DNA
<213> ORGANISM: Artificial Sequence
<220> FEATURE:
<223> OTHER INFORMATION: Synthetic

<400> SEQUENCE: 116
tgcgtgtccc tgcatgcatc taaccct                               27

<210> SEQ ID NO 117
<211> LENGTH: 27
<212> TYPE: DNA
<213> ORGANISM: Artificial Sequence
<220> FEATURE:
<223> OTHER INFORMATION: Synthetic

<400> SEQUENCE: 117
tgcgtgtccc tgcatgcatc cctaacc                               27

```
<210> SEQ ID NO 118
<211> LENGTH: 27
<212> TYPE: DNA
<213> ORGANISM: Artificial Sequence
<220> FEATURE:
<223> OTHER INFORMATION: Synthetic

<400> SEQUENCE: 118
tgcgtgtccc tgcatgcatc ctaaccc                                27

<210> SEQ ID NO 119
<211> LENGTH: 27
<212> TYPE: DNA
<213> ORGANISM: Artificial Sequence
<220> FEATURE:
<223> OTHER INFORMATION: Synthetic

<400> SEQUENCE: 119
tgcgtgtccc tgcatgcatc aacccta                                27

<210> SEQ ID NO 120
<211> LENGTH: 27
<212> TYPE: DNA
<213> ORGANISM: Artificial Sequence
<220> FEATURE:
<223> OTHER INFORMATION: Synthetic

<400> SEQUENCE: 120
tgcgtgtccc tgcatgcatc accctaa                                27

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
tgcctgcatg tgtccgcatc                                        20

<210> SEQ ID NO 122
<211> LENGTH: 27
<212> TYPE: DNA
<213> ORGANISM: Artificial Sequence
<220> FEATURE:
<223> OTHER INFORMATION: Synthetic

<400> SEQUENCE: 122
tgcctgcatg tgtccgcatc ccctaac                                27

<210> SEQ ID NO 123
<211> LENGTH: 27
<212> TYPE: DNA
<213> ORGANISM: Artificial Sequence
<220> FEATURE:
<223> OTHER INFORMATION: Synthetic

<400> SEQUENCE: 123
tgcctgcatg tgtccgcatc taaccct                                27

<210> SEQ ID NO 124
<211> LENGTH: 27
<212> TYPE: DNA
<213> ORGANISM: Artificial Sequence
<220> FEATURE:
<223> OTHER INFORMATION: Synthetic
```

```
<400> SEQUENCE: 124
tgcctgcatg tgtccgcatc cctaacc                                              27

<210> SEQ ID NO 125
<211> LENGTH: 27
<212> TYPE: DNA
<213> ORGANISM: Artificial Sequence
<220> FEATURE:
<223> OTHER INFORMATION: Synthetic

<400> SEQUENCE: 125
tgcctgcatg tgtccgcatc ctaaccc                                              27

<210> SEQ ID NO 126
<211> LENGTH: 27
<212> TYPE: DNA
<213> ORGANISM: Artificial Sequence
<220> FEATURE:
<223> OTHER INFORMATION: Synthetic

<400> SEQUENCE: 126
tgcctgcatg tgtccgcatc aacccta                                              27

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
tgcctgcatg tgtccgcatc accctaa                                              27

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
tgctccgcac tgcatgtgtc                                                      20

<210> SEQ ID NO 129
<211> LENGTH: 27
<212> TYPE: DNA
<213> ORGANISM: Artificial Sequence
<220> FEATURE:
<223> OTHER INFORMATION: Synthetic

<400> SEQUENCE: 129
tgctccgcac tgcatgtgtc ccctaac                                              27

<210> SEQ ID NO 130
<211> LENGTH: 27
<212> TYPE: DNA
<213> ORGANISM: Artificial Sequence
<220> FEATURE:
<223> OTHER INFORMATION: Synthetic

<400> SEQUENCE: 130
tgctccgcac tgcatgtgtc taaccct                                              27

<210> SEQ ID NO 131
<211> LENGTH: 27
```

-continued

<212> TYPE: DNA
<213> ORGANISM: Artificial Sequence
<220> FEATURE:
<223> OTHER INFORMATION: Synthetic

<400> SEQUENCE: 131
tgctccgcac tgcatgtgtc cctaacc                                          27

<210> SEQ ID NO 132
<211> LENGTH: 27
<212> TYPE: DNA
<213> ORGANISM: Artificial Sequence
<220> FEATURE:
<223> OTHER INFORMATION: Synthetic

<400> SEQUENCE: 132
tgctccgcac tgcatgtgtc ctaaccc                                          27

<210> SEQ ID NO 133
<211> LENGTH: 27
<212> TYPE: DNA
<213> ORGANISM: Artificial Sequence
<220> FEATURE:
<223> OTHER INFORMATION: Synthetic

<400> SEQUENCE: 133
tgctccgcac tgcatgtgtc aacccta                                          27

<210> SEQ ID NO 134
<211> LENGTH: 27
<212> TYPE: DNA
<213> ORGANISM: Artificial Sequence
<220> FEATURE:
<223> OTHER INFORMATION: Synthetic

<400> SEQUENCE: 134
tgctccgcac tgcatgtgtc accctaa                                          27

<210> SEQ ID NO 135
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 135
nnnntgctcc gtgcatctgg catc                                             24

<210> SEQ ID NO 136
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 136
nnnntgctcg cgtacctgtg catc                                             24

<210> SEQ ID NO 137

```
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 137
nnnntgcgca ctgcatgtgt cctc                                              24

<210> SEQ ID NO 138
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 138
nnnntgcgtg tccctgcatg catc                                              24

<210> SEQ ID NO 139
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 139
nnnntgcctg catgtgtccg catc                                              24

<210> SEQ ID NO 140
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 140
nnnntgctcc gcactgcatg tgtc                                              24

<210> SEQ ID NO 141
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 141
nnnnctgaac tcaccgcgac gtctgt                                            26
```

```
<210> SEQ ID NO 142
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: n is a, c, g, or t

<400> SEQUENCE: 142
nnnnaggagg gcgtggatat gtcctgcgg                                29

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
tcctgactat gcgggtatga                                          20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
ccttcatcac gagaacggat                                          20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
tgatcagtca acgggggaca                                          20

<210> SEQ ID NO 146
<211> LENGTH: 21
<212> TYPE: DNA
<213> ORGANISM: Artificial Sequence
<220> FEATURE:
<223> OTHER INFORMATION: Synthetic

<400> SEQUENCE: 146
ttcgagaggt cctttcacc a                                         21
```

ASSAY FOR TELOMERE LENGTH REGULATORS

CROSS-REFERENCE TO RELATED APPLICATIONS

This application is a 35 USC § 371 National Stage application of International Application No. PCT/US2016/023114 filed Mar. 18, 2016, which claims the benefit under 35 USC § 119(e) to U.S. Application Ser. No. 62/184,148 filed Jun. 24, 2015 and to U.S. Application Ser. No. 62/135,616 filed Mar. 19, 2015. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant No. R37AG009383 awarded by the National Institutes of Health. The government has certain rights in the invention.

INCORPORATION OF SEQUENCE LISTING

This application contains a sequence listing. It has been submitted electronically via EFS-Web as an ASCII text file entitled "P13359-03 ST25.txt." The sequence listing is 28,173 bytes in size, and was created on Mar. 16, 2020. It is hereby incorporated by reference in its entirety.

BACKGROUND OF THE INVENTION

Field of the Invention

The invention relates generally to chromosome maintenance and cell viability, and more specifically to an assay for identifying telomere length regulators.

Background Information

Telomeres are genetic elements located at the ends of all eukaryotic chromosomes that preserve genome stability and cell viability by preventing aberrant recombination and degradation of DNA. In humans, the telomeric sequence is composed of 10-20 kilobases of TTAGGG repeats. There is increasing evidence that gradual loss of telomeric repeat sequences may be a timing ("clock") mechanism limiting the number of cellular divisions in normal somatic cells. In contrast, immortal cells can maintain a stable telomere length by telomere addition by telomerase, a ribonucleoprotein enzyme that is able to add TTAGGG repeats to the ends of chromosomes.

Telomere length is maintained during cell division through the action of telomerase, which is a unique reverse transcriptase that elongates telomeric DNA. Telomerase is relatively abundant in germline, stem cells and embryonic tissues, inflammatory cells, proliferative cells of renewal tissues, as well as cancer cells. In contrast, telomerase activity is difficult to detect in normal somatic human tissues. The correlation of telomerase activity and cellular replication has prompted the association of telomerase and cancer. Telomerase activity has been found in approximately 85% of human cancers. Thus, it has been proposed that up-regulation or re-expression of telomerase may be a critical event responsible for continuous tumor cell growth.

The telomerase enzyme is made up of an essential core as well as several accessory proteins. The core telomerase consists of the RNA component (Telomerase RNA, TR) and the catalytic subunit (Telomerase Reverse Transcriptase, TERT). The structure of the RNA component is conserved from ciliates to humans, while the sequence is not. In the ciliate Tetrahymena the RNA is 150-200 nucleotides (nt) in length while in mammalian cells, the RNA component is significantly larger, 390-450 nt. The catalytic TElomerase Reverse Transcriptase (TERT) component, first identified in the ciliate Euplotes, has homologues in yeast (EST 2), human (hTERT), and mouse (mTERT) and most other eukaryotes. TERT contains sequence motifs similar to reverse transcriptase, and mutations of essential aspartate residues that are conserved in the catalytic triad of reverse transcriptases eliminate telomerase activity. Minimal telomerase activity can be reconstituted in an in vitro transcription/translation extract using TERT and TR components, indicating that these are sufficient for catalysis.

Given the association of telomerase activity with cancer and age related degenerative diseases, telomerase activity is important in clinical settings. Several analytical procedures for the quantification of telomerase activity have been reported. Methods for detecting telomerase activity, as well as for identifying compounds that regulate or affect telomerase activity, have been described. See PCT Pat. App. Pub. No. 93/23572 and U.S. Pat. Nos. 5,629,154, 5,648,215, 5,645,986, 5,695,932 and 5,489,508. Each of the foregoing patent publications is incorporated herein by reference.

The most frequently utilized assay is Telomeric Repeat Amplification Protocol (TRAP), which is a two stage PCR-based assay. In the first stage, telomerase adds 5'-TTAGGG-3' repeats to the end of a synthetic primer. In the second stage, the extended oligonucleotide products are amplified using a reverse primer. When visualized by autoradiography, a positive test by TRAP shows a ladder of bands. The band volume can then be quantified. TRAP is time consuming, labor intensive, PCR-dependent and susceptible to inhibition by extracts of clinical samples. Furthermore, it is difficult to quantify telomerase activity because of logarithmic amplification of telomerase products in the PCR amplification step, which is subject to false positive results. The susceptibility of the TRAP assay to Taq-polymerase inhibitors can result in the production of false negative results.

A similar telomerase assay that replaced the electrophoretic step of the TRAP assay with an ELISA detection system has been developed. This system is also PCR-dependent although the ELISA detection method appears to offer no clear advantage over the traditional TRAP. In an effort to eliminate technical issues associated with TRAP, in situ hybridization assays for the quantification of human Telomerase (hTR) RNA and human Telomerase Reverse Transcriptase (hTERT) mRNA were developed. However, hTR and hTERT expression does not necessarily equate to telomerase activity.

Another telomerase assay is disclosed in PCT/IL01/00808 (WO 02/20838). This assay uses rotating quinone-functionalized magnetic beads to generate H2O2 within the assay. The endogenous production of H2O2 putatively overcomes the problem of luminol being sparingly soluble in aqueous buffer solutions. However, the rotating magnetic beads reduces the ability to develop high throughput screening protocols and may impact on the sensitivity depending on the length of oligonucleotide primer employed.

Researchers have stated that that the amount and length of telomeric DNA in human fibroblasts decreases as a function of serial passage during aging in vitro, and possibly in vivo.

It was later shown that this telomere shortening causes cellular senescence. They also state that tumor cells are characterized by shortened telomeres and increased frequency of aneuploidy, including telomeric associations. Since the loss of telomeric DNA ultimately causes cell-cycle arrest in normal cells, the final steps in this process may block growth in immortalized cells. Whereas normal cells with relatively long telomeres and a senescent phenotype may contain little or no telomerase activity, tumor cells with short telomeres may have significant telomerase activity. Telomerase may therefore be an effective target for antitumor drugs. There are a number of possible mechanisms for loss of telomeric DNA during ageing, including incomplete replication, degradation of termini (specific or nonspecific), and unequal recombination coupled to selection of cells with shorter telomeres.

Long-term cell viability is critically dependent on maintenance of telomere length. In humans, syndromes of telomere shortening cause age-related degenerative diseases that are often fatal. At the cellular level, the loss of tissue renewal that contributes to these diseases is caused by short telomeres inducing apoptosis or cellular senescence. On the other hand, cancer cells avoid cell death by increasing or maintaining telomere lengths. Telomere shortening occurs during normal cell division because DNA replication fails to copy the very end of the chromosome. Telomerase adds telomere repeats onto chromosome ends to balance the shortening that occurs due to replication. The delicate balance of shortening and lengthening is regulated by an intricate series of feedback mechanisms to establish a robust telomere length equilibrium.

Telomere length maintenance is essential for cell viability. Telomere shortening that occurs during cell division is balanced by telomerase, which adds telomere repeats onto chromosome ends. The delicate balance of shortening and lengthening is regulated by an intricate series of feedback mechanisms that establish a dynamic telomere length equilibrium. In humans, syndromes of telomere shortening cause age-related degenerative diseases including dyskeratosis congenita, pulmonary fibrosis, aplastic anemia and others. Elucidating the molecular interactions that regulate telomere elongation is essential to understand telomere function and how it is disrupted in disease.

In both yeast and human cells, short telomeres induce either senescence or apoptosis through activation of the DNA damage response. Similarly in telomerase negative mTR$^{-/-}$ mice, or in Telomerase heterozygous mice mTR+/−, after four to five generations of interbreeding, cells with short telomeres undergo apoptosis or cellular senescence. The short telomeres are the cause of this apoptosis or cellular senescence, since it occurs even when some telomerase is present. This cell loss can either contribute to age-related disease or can limit the tumor growth in vivo.

The ATM and ATR kinase-dependent DNA damage response pathways are activated in primary human cells when telomeres are critically short. Induction of telomere dysfunction through a different mechanism, the removal of shelterin components, also activates ATM or ATR-dependent signaling. Which pathway is activated is dependent on which shelterin component is removed. Deletion of TRF1 activates the ATM pathway while removal of POT1 primarily activates the ATR pathway.

The role of ATM in regulating telomere elongation in mammalian cells has been more controversial than in yeast. In human cells, a prominent, early paper suggested that ATM plays no role in human telomere maintenance. However other reports suggested cells might have shorter telomeres in the absence of ATM. The different methods for measuring telomeres and the small number of samples analyzed left this unresolved. Mouse studies on ATM and telomere elongation have also failed to find a definitive role for ATM. To detect telomere shortening in the absence of telomerase, it requires four to six generations of interbreeding telomerase null mice. Two groups, including our own, showed that first generation ATM null mice do not have short telomeres. Progressive breeding of ATM$^{+/-}$ heterozygotes did not show telomere shortening. However, to detect telomere shortening in telomerase null mice, four to six generations of progressive breeding is required. Since ATM$^{-/-}$ mice are sterile, it is not possible to interbreed them to examine telomere length over many generations. Thus, the failure to see short telomeres in these mice might be simply due to the limitations of breeding. In addition, as discussed below, ATM and ATR play partially overlapping roles in several species, thus to see major changes in telomere length in mice may require reduction in both pathways.

The ATM protein kinase is a central regulator of the cellular response to DNA damage and the response to telomere dysfunction. After recognition of damage, ATM signals cell cycle arrest and induction of repair pathways. Ataxia telangiectasia (AT) patients, who lack ATM function, have immune system defects, neurological impairment, are cancer prone and radiosensitive. A role for ATM in telomere length maintenance was suggested when the ATM gene was cloned and shown to be the homolog of the yeast Tel1 gene. In yeast, loss of Tel1$^{ATM}$ function leads to short telomeres. However, there have been conflicting results regarding the role of ATM in regulating telomere elongation in mammalian cells. In human cells, a prominent, early paper suggested that ATM plays no role in human telomere maintenance. However, other reports suggested cells might have shorter telomeres in the absence of ATM. Modification of human TRF1 protein by both ATM and tankyrase regulates binding of TRF1 to the telomere; however, this regulation of TRF1 is not conserved in mice.

At the cellular level, the loss of tissue renewal is caused by short telomeres that activates a DNA damage response, resulting in apoptosis or senescence. Critically short telomeres activate the ATM and ATR kinase-dependent pathways in primary human cells, leading to senescence. In addition, induction of telomere dysfunction through the removal of shelterin components also activates ATM or ATR dependent signaling and cell cycle arrest. Cancer cells avoid cell death through increased telomerase expression or other mechanisms that maintain telomere length.

While there has been significant progress and ongoing studies to understand the role of ATM and ATR in telomere dysfunction, less is known about the role of these kinases in normal telomere elongation, when telomeres are not critically short. A role for ATM in telomere length maintenance was first evident when the ATM gene was cloned and shown to be the homolog of the Tel1 gene in yeast. Loss of Tel1$^{ATM}$ function leads to short telomeres. Interestingly, while deletion of the related kinase Mec1$^{ATR}$ does not itself cause telomeres shortening, the double mutant of Tel1$^{ATM}$ Mec1$^{ATR}$ shows further shortening not seen in Tel1$^{ATM}$ mutant alone. This implies that Mec1$^{ATR}$ may partially compensate for the loss of Tel1$^{ATM}$.

Given the conserved role of ATM in telomere length regulation in *S. cerevisiae, S. pombe*, and *Arabidopsis*, the role of ATM kinase in telomere elongation in mammalian cells was revisited. To avoid the issues of breeding ATM$^{-/-}$ mice and missing small effects of telomere length changes on long telomeres, an in vivo telomere elongation assay was developed where telomerase repeat addition can be monitored over 48 hours. The assay is called ADDIT (Addition of de novo initiated telomeres) and measures telomere addition at a single chromosome end.

SUMMARY OF THE INVENTION

The present invention is based on the seminal discovery of an assay that can identify genes required for telomerase-dependent telomere elongation by measuring the de novo telomere addition at a single chromosome. Here, the successful development of a de novo telomere elongation assay in mouse cells is reported. The assay is used to demonstrate that ATM kinase pathway regulates the elongation of telomeres by telomerase. This highlights the conserved nature of the pathways that regulate telomere length across species and suggests novel approaches to manipulating telomere length. An illustrative schematic of the screening assay of the invention is provided in the Examples.

The present invention relates to a method of identifying a regulator of telomere length which includes a) culturing a mammalian cell comprising a modified chromosome containing an internal telomere seed sequence and an endonuclease cleavage site downstream of the telomere seed sequence, wherein the cell conditionally expresses an endonuclease that cleaves and exposes the telomere seed sequence; b) contacting the cell of (a) with an agent that modulates expression of a selected gene or pathway in the cell; and c) measuring de novo telomere addition to the seed sequence in the presence and absence of the agent, wherein addition of telomere sequence in the presence of the agent, but not in the absence of the agent, and the degree of addition, is indicative of identification of the agent as being a regulator of telomere length, thereby identifying a regulator of telomere length.

In one aspect, the measuring of c), above, is by a technique including PCR, such as a modified single telomere length analysis (STELA) or by PCR followed by nucleotide sequencing. In one aspect, the agent that stimulates cleavage of the chromosome at the cleavage site is a tetracycline such as doxycycline. In another aspect, the agent that affects expression of a selected gene or pathway in the cell is selected from a small molecule, a peptide, a nucleic acid molecule, or a protein. For example, the nucleic acid molecule is an antisense or a siRNA molecule. One of the advantages of the present invention is that the screening can be performed after one cell cycle, e.g., 48 hours.

In some embodiments, the pathway is a kinase pathway, for example, the pathway is the ataxia telangiectasia mutated (ATM) kinase pathway or a cyclin dependent kinase pathway.

In another aspect, the invention provides an isolated mammalian cell line characterized by genome including a modified chromosome containing a telomere seed sequence and an endonuclease cleavage site downstream of the telomere seed sequence, wherein conditional cleavage of at the cleavage site will allow de novo elongation of the seed sequence. The cells are preferably mammalian cells, including murine or human cells. In an illustrative example provided herein the modified chromosome is mouse chromosome 4.

In yet another aspect, the invention provides a kit which includes cells of the mammalian cell line of the invention along with reagents for culturing the cells. The kit may further include reagents for measuring de novo telomere addition.

BRIEF DESCRIPTION OF THE DRAWINGS

FIGS. 3A-3C are pictorial and graphical representations showing that de novo telomere addition occurs only in telomerase-positive cells. FIG. 3C includes SEQ ID NOs: 1-10 (ordered from top to bottom).

FIGS. 5A-5B are pictorial representations showing classifications of de novo telomere addition. FIG. 5A includes SEQ ID NOS: 11-16 and FIG. 5B includes SEQ ID NOS: 17-34 (ordered from top to bottom).

FIG. 8A-8B are pictorial and graphical representations, respectively, showing that inhibition of ATM blocks de novo telomere addition. FIG. 8C includes SEQ ID NOs: 35-51 (ordered from top to bottom).

FIGS. 10A-10C are pictorial and graphical representations showing that de novo telomere addition occurs in G2/M phase.

DETAILED DESCRIPTION OF THE INVENTION

Figure 1A:
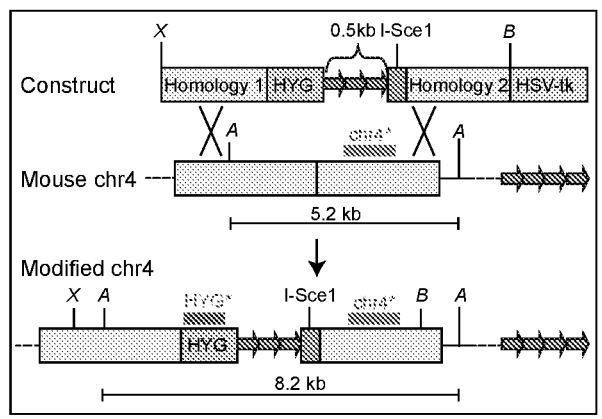
FIGS. 1A-1B are pictorial representations relating to generation of a cell line to assay de novo telomere addition.

The present invention is based on discovery of an assay that can identify genes required for telomerase-dependent telomere elongation by measuring the de novo telomere addition at a single chromosome over just one cell cycle.

Before the present compositions and methods are further described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention describes a new assay, named ADDIT, that can identify genes required for telomerase-dependent telomere elongation by measuring the de novo telomere addition at a single chromosome. Using this assay, the inventors show that the ATM kinase pathway and the cyclin dependent kinase pathway utilized in the cell cycle are required for telomerase-mediated telomere addition. Activation of ATM and cyclin dependent kinase 1 was shown to cause telomere elongation. Using an independent approach, they also found that inhibition of ATM kinase activity prevented bulk telomere elongation by telomerase and activation of ATM caused telomere elongation in cell culture experiments assayed by Southern blot.

The mechanism of telomere length maintenance involves many inter-dependent regulatory pathways that act together to establish length homeostasis. This process involves the interaction of telomere binding proteins such as shelterin with telomerase to regulate elongation. In addition to dedicate telomere binding proteins, DNA damage proteins including MRN complex and Ku are conserved players in length maintenance from yeast to mammals. Protein modification also plays a key role in regulating telomere length. It is demonstrated that one of the key regulators of telomere length, ATM kinase pathway, is also conserved from yeast to mammalian system. It is well documented that ATM is required for normal telomere maintenance in different yeast species including S. pombe in which ATM mediates the telomerase recruitment. ATM homologue in Arabidopsis also plays a role regulating telomere lengths by promoting elongation of short telomeres. Drosophila telomeres do not use telomerase for telomere length maintenance, yet remarkably the role of ATM is conserved in telomere function. It suggests that even when telomerase was lost from this evolutionary branch of Diptera, the process that regulate telomere length was still retained.

ATR may compensate for loss of ATM.

Data from both the ADDIT assay and Southern analysis suggests ATM kinase is required for telomere length maintenance. When ATM was inhibited by siRNA different results were seen in ADDIT assay and the longer term bulk culture experiment: telomere addition was completely blocked in ADDIT assay but not when cells were grown continuously in culture. This difference may be due to the transient siATM knockdown that does not sufficiently block ATM in longer-term culture conditions. Another possibility is that ATR kinase may compensate for ATM loss in the longer-term culture experiments. Previous studies in S. cerevisiae suggest ATR plays a minor, yet critical role in telomere maintenance. Cells lacking Tel1$^{ATM}$ are completely defective in telomere extension within the first few hours after the creation of short telomere. The bulk telomere lengths of tel1$^{ATM\Delta}$ cells are short yet stable. Progressive telomere shortening is only seen when both Tel1$^{ATM}$ and Mec1$^{ATR}$ are deleted, suggesting Mec1$^{ATR}$ may play some role in telomere elongation when Tel1$^{ATM}$ is missing. Similar to S. cerevisiae, the shortest telomere phenotype of S. pombe was seen in the Rad3$^{ATR}$/Tel1$^{ATM}$ double mutants. Interestingly, Rad3$^{ATR}$ mutant cells have shorter telomere lengths compared to Tel1$^{ATM}$, indicating Rad3$^{ATR}$ play more critical role in telomere length regulation than does S. pombe Tel1$^{ATM}$.

Previous studies in mice indicated that ATM is not required for specific rescue and elongation of the shortest telomeres. Briefly, the ATM$^{+/-}$ mice were crossed to mTR$^{-/-}$ G5 late generation mice with short telomeres. In the F1 mice that resulted, shortest signal free ends were rescued in both ATM$^{+/-}$ and ATM$^{-/-}$ offspring, suggesting ATM is not essential for elongation of the shortest telomeres. This elongation, however, may be due to ATR compensating for the loss of ATM. The role of the ATR kinase in these pathways has not been examined as ATR null mice are lethal. Ataxia telangiectasia (AT) patients with mutations in the ATM gene have shorter telomeres compared to their age-matched controls, but not as short as other patients with telomerase mutations. This observation suggests ATR may also compensate for the loss of ATM function in telomere length maintenance in human. Dissecting the mechanism of telomere shortening in AT patients may have implications for individualized treatment plans. It is important to understand whether short telomeres can directly contribute to a more severe AT clinical phenotype and if telomere could be a potential therapeutic target.

Possible mechanisms of ATM regulated telomere elongation.

Previous findings in S. cerevisiae imply that the primary function of ATM in telomere maintenance is by modulating the access of telomerase to its substrate, telomere, rather than by altering the enzyme activity level of telomerase. The kinase activity of ATM is required for telomere maintenance as kinase dead mutant show short telomeres. While specific ATM substrates that affect telomere length have been characterized in S. pombe, the key substrates in S. cerevisiae are still controversial. In S. pombe, Tel1$^{ATM}$ and/or Rad3$^{ATR}$ phosphorylate a shelterin component Ccq1 that then interacts with telomerase subunit Est1 to mediate telomerase recruitment. In S. cerevisiae, while Tel1$^{ATM}$ can phosphorylate the single-strand telomere binding protein Cdc13, this phosphorylation apparently is not responsible for recruitment of Est1. While the precise functional homologues of Ccq1 and Est1 in mammalian cell are not fully established likely due to sequence divergence and/or convergent evolution, shelterin components are still excellent candidates for ATM substrates in mammals given the conservation of length maintenance mechanisms across phyla. Previous studies in human cells suggest ATM phosphorylation of TRF1 can alter TRF1 association with telomeres, which can affect length regulation as well as end protection. Further, identification of ATM kinase target(s) will help to understand how ATM regulates telomerase recruitment and telomere elongation in mammalian cells.

Most of the key players and requirements for telomere length regulation have been investigated in the model organism S.cerevisiae, including cyclin-dependent kinase (Cdk). Cdks are serine/theornine kinases responsible for various cellular processes such as cell cycle progression and transcription. In both S.cerevisiae and S.pombe, a single Cdk, Cdk1, is responsible for regulating cell cycle transitions. In addition to its critical role in cell cycle regulation, a previous study from our lab showed that Cdk1 is required for telomere elongation by regulating the generation of the 3' overhang. In higher eukaryotes, there are a growing number of Cdk family members identified. Functional characterization of these Cdks elucidated specific roles in different cellular processes such as cell cycle regulation, transcription and others, but the role in telomere length regulation is not well elucidated.

The examples herein illustrate that telomerase-mediated telomere addition is regulated in a cell-cycle dependent manner in mammalian cells, and that mammalian Cdks, including Cdk1, are required for telomere elongation in vivo.

The essential role of Cdk1 in telomere addition.

Previous studies have shown that many of the key regulators required for telomere length maintenance are identical between the natural telomeres and de novo telomere ends. The yeast Cdk1 activity is also required to generate the 3' G-rich overhang, which is important for telomere length maintenance, at both de novo telomere ends as well as the natural telomeres. It is possible that Cdk1 activates a nuclease(s) that is involved in single-strand resection, such as Mre11 that is involved in resection at double-strand DNA break sites. In yeast, Cdk1 phosphorylates the nuclease Dna2, which is involved in generating the 3' overhang at telomeres. It will be interesting to find whether mammalian Cdk1 is also responsible for generating the 3' overhang by activating a nuclease(s) responsible for 5' strand resection.

In addition, Cdk1 appears to be involved in regulating telomerase recruitment. The results from ADDIT assay shown the examples demonstrated that Cdk1 activity is required for de novo telomere addition in mammalian cells, indicating the conserved role of Cdk1 in telomere length regulation in higher eukaryotes.

ADDIT assay may allow dissection of new pathways of telomere length regulation.

The ADDIT assay described here will allow rapid dissection of the ATM pathway of telomere length regulation in addition to identification of new regulators of telomere length. The very brief time of 48 hrs required for the ADDIT assay allows the identification of essential genes that are difficult to probe for roles in telomere length regulation with the conventional method of long-term cell growth. The ADDIT assay was designed in mouse CASTEiJ cells that have telomere length and distribution very similar to humans, in contrast to standard laboratory strains. This allows functional probing of telomeres in a setting similar to human telomere length regulation. The assay will provide insights into telomere length homeostasis and may possibly identify potential targets for future therapeutics.

As such, the present provides to a method of identifying a regulator of telomere length which includes a) culturing a mammalian cell comprising a modified chromosome containing an internal telomere seed sequence and an endonuclease cleavage site downstream of the telomere seed sequence, wherein the cell conditionally expresses an endonuclease that cleaves and exposes the telomere seed sequence; b) contacting the cell of (a) with an agent that modulates expression of a selected gene or pathway in the cell; and c) measuring de novo telomere addition to the seed sequence in the presence and absence of the agent, wherein addition of telomere sequence in the presence of the agent, but not in the absence of the agent, and the degree of addition, is indicative of identification of the agent as being a regulator of telomere length, thereby identifying a regulator of telomere length.

In one aspect, the measuring of c), above, is by a technique including PCR, such as a modified single telomere length analysis (STELA) or by PCR followed by nucleotide sequencing. STELA was developed in 2003 by Duncan Baird. This technique may be incorporated as a part of the ADDIT assay. This technique allows investigations that can target specific telomere ends, which is not possible with TRF analysis described below.

Several techniques may be employed to assess average telomere length in eukaryotic cells. The most widely used method is the Terminal Restriction Fragment (TRF) Southern blot, which involves hybridization of a radioactive $^{32}$P-(TTAGGG)n oligonucleotide probe to restriction enzyme digested genomic DNA embedded on a nylon membrane and subsequently exposed to autoradiographic film or phosphoimager screen. Another histochemical method, termed Q-FISH, involves fluorescent in situ hybridization (FISH).

The present invention describes agents, such as chemical compounds or nucleic acid molecules, and the assay used for their identification, that modulate de novo telomere addition by affecting a gene or pathway implicated in telomere extension via telomerase, such as a kinase pathway, for example, the ATM kinase pathway or a cyclin dependent kinase pathway active in cell cycling.

As used herein, an agent identified as a regulator of telomere length acts to increase extension of telomeres. The agent may interact directly with a gene promoter to effectuate an increase or decrease in transcription or the agent may interact in a number of other ways to indirectly increase telomere addition. For example, the agent may activate a particular signal transduction pathway leading to increased or decreased transcription of a gene. Alternatively, the agent may act to suppress repressors of transcription by direct binding to the transcriptional repressor thus blocking binding of the repressor to a promoter. Alternatively, the agent may act indirectly to suppress transcriptional repressors or increase transcription.

Agents to be screened encompass numerous chemical classes, though typically they are chemical compounds, such as an organic molecule, and often oligonucleotides or small organic compounds (i.e., small molecules) having a molecular weight of more than 100 Daltons and less than about 2,500 Daltons. Test agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one aspect, an agent for use in with the present invention is a polynucleotide, such as an antisense oligonucleotide or RNA molecule. In various aspects, the agent may be a polynucleotide, such as an antisense oligonucleotide or RNA molecule, such as microRNA, dsRNA, siRNA, stRNA, and shRNA.

MicroRNAs (miRNA) are single-stranded RNA molecules, which regulate gene expression. miRNAs are encoded by genes from whose DNA they are transcribed but miRNAs are not translated into protein; instead each primary transcript (a pri-miRNA) is processed into a short stem-loop structure called a pre-miRNA and finally into a functional miRNA. Mature miRNA molecules are either fully or partially complementary to one or more messenger RNA (mRNA) molecules, and their main function is to down-regulate gene expression. MicroRNAs can be encoded by independent genes, but also be processed (via the enzyme Dicer) from a variety of different RNA species, including introns, 3' UTRs of mRNAs, long noncoding RNAs, snoR-NAs and transposons. As used herein, microRNAs also include "mimic" microRNAs which are intended to mean a microRNA exogenously introduced into a cell that have the same or substantially the same function as their endogenous counterpart. Thus, while one of skill in the art would understand that an agent may be an exogenously introduced RNA, an agent also includes a compound or the like that increase or decrease expression of microRNA in the cell.

The terms "small interfering RNA" and "siRNA" also are used herein to refer to short interfering RNA or silencing RNA, which are a class of short double-stranded RNA molecules that play a variety of biological roles. Most notably, siRNA is involved in the RNA interference (RNAi) pathway where the siRNA interferes with the expression of a specific gene. In addition to their role in the RNAi pathway, siRNAs also act in RNAi-related pathways (e.g., as an antiviral mechanism or in shaping the chromatin structure of a genome).

Polynucleotides of the present invention, such as antisense oligonucleotides and RNA molecules may be of any suitable length. For example, one of skill in the art would understand what lengths are suitable for antisense oligonucleotides or RNA molecule to be used to regulate gene expression. Such molecules are typically from about 5 to 100, 5 to 50, 5 to 45, 5 to 40, 5 to 35, 5 to 30, 5 to 25, 5 to 20, or 10 to 20 nucleotides in length. For example the molecule may be about 5, 10, 15, 16, 17, 18, 19, 20, 21, 22, 23, 24, 25, 26, 27, 28, 29, 30, 31, 32, 33, 34, 35, 40, 45 or 50 nucleotides in length. Such polynucleotides may include from at least about 15 to more than about 120 nucleotides, including at least about 16 nucleotides, at least about 17 nucleotides, at least about 18 nucleotides, at least about 19 nucleotides, at least about 20 nucleotides, at least about 21 nucleotides, at least about 22 nucleotides, at least about 23 nucleotides, at least about 24 nucleotides, at least about 25 nucleotides, at least about 26 nucleotides, at least about 27 nucleotides, at least about 28 nucleotides, at least about 29 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, at least about 100 nucleotides, at least about 110 nucleotides, at least about 120 nucleotides or greater than 120 nucleotides.

The term "polynucleotide" or "nucleotide sequence" or "nucleic acid molecule" is used broadly herein to mean a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the terms as used herein include naturally occurring nucleic acid molecules, which can be isolated from a cell, as well as synthetic polynucleotides, which can be prepared, for example, by methods of chemical synthesis or by enzymatic methods such as by the polymerase chain reaction (PCR). It should be recognized that the different terms are used only for convenience of discussion so as to distinguish, for example, different components of a composition.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. Depending on the use, however, a polynucleotide also can contain nucleotide analogs, including non-naturally occurring synthetic nucleotides or modified naturally occurring nucleotides. Nucleotide analogs are well known in the art and commercially available, as are polynucleotides containing such nucleotide analogs. The covalent bond linking the nucleotides of a polynucleotide generally is a phosphodiester bond. However, depending on the purpose for which the polynucleotide is to be used, the covalent bond also can be any of numerous other bonds, including a thiodiester bond, a phosphorothioate bond, a peptide-like bond or any other bond known to those in the art as useful for linking nucleotides to produce synthetic polynucleotides.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

In various embodiments antisense oligonucleotides or RNA molecules include oligonucleotides containing modifications. A variety of modification are known in the art and contemplated for use in the present invention. For example oligonucleotides containing modified backbones or non-natural internucleoside linkages are contemplated. As used herein, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In various aspects modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Certain oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

In various aspects modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In various aspects, oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. In various aspects, oligonucleotides may include phosphorothioate backbones and oligonucleosides with heteroatom backbones. Modified oligonucleotides may also contain one or more substituted sugar moieties. In some embodiments oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$ and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, N3, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Another modification includes 2'-methoxyethoxy (2'$OCH_2CH_2OCH_3$, also known as 2'-O-(2-methoxyethyl) or 2'-MOE).

In one embodiment, an agent features a chemically modified nucleic acid molecule that includes one or more chemical modifications described herein. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5'-C-methyl nucleotides, and terminal glyceryl and/or inverted deoxy abasic residue incorporation. These chemical modifications are shown to preserve activity in cells while at the same time, dramatically increasing the serum stability of these compounds. In one aspect, the chemically modified nucleotide used in the invention includes a 2'-deoxyribonucleotide, 2'-O-methyl ribonucleotide, 2'-fluoro ribonucleotide, 2'-amino ribonucleotide, 2'-O-amino ribonucleotide, 2'-C-allyl ribonucleotide, 2'-O-allyl ribonucleotide, 2'-methoxyethyl ribonucleotide, 5'-C-methyl ribonucleotide, or a combination thereof. In another aspect, the chemically modified oligonucleotide used in the invention includes a 2'-deoxyribonucleotide, 2'-O-methyl ribonucleotide, 2'-fluoro ribonucleotide, 2'-amino ribonucleotide, 2'-O-amino ribonucleotide, 2'-C-allyl ribonucleotide, 2'-O-allyl ribonucleotide, 2'-methoxyethyl ribonucleotide, 5'-C-methyl ribonucleotide, or a combination thereof.

In a non-limiting example, the introduction of chemically modified nucleotides into nucleic acid molecules provides a powerful tool in overcoming potential limitations of in vivo stability and bioavailability inherent to native RNA molecules that are delivered exogenously. For example, the use of chemically modified nucleic acid molecules can enable a lower dose of a particular nucleic acid molecule for a given therapeutic effect since chemically modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically modified nucleic acid molecule is reduced as compared to a native nucleic acid molecule, for example, when compared to a native unmodified nucleic acid molecule, the overall activity of the modified nucleic acid molecule can be greater than that of the native molecule due to improved stability and/or delivery of the molecule.

In related aspects, the present invention includes use of Locked Nucleic Acids (LNAs) to generate antisense nucleic acids having enhanced affinity and specificity for the target polynucleotide. LNAs are nucleic acid in which the 2'-hydroxyl group is linked to the 3' or 4' carbon atom of the sugar ring thereby forming a bicyclic sugar moiety. The linkage is preferably a methelyne ($—CH_2—)_n$ group bridging the 2' oxygen atom and the 4' carbon atom wherein n is 1 or 2.

Other modifications include 2'-methoxy(2'-O—$CH_3$), 2'-aminopropoxy(2'-$OCH_2CH_2CH_2NH_2$), 2'-allyl (2'-CH—CH—$CH_2$), 2'-O-allyl (2'-O—$CH_2$—CH—$CH_2$), 2'-fluoro (2'-F), 2'-amino, 2'-thio, 2'-Omethyl, 2'-methoxymethyl, 2'-propyl, and the like. The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine, 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazi-n-2 (3H)-one), phenothiazine cytidine (1H-pyrimido[5,4-b][1,4] benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrimido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases are known in the art. Certain of these nucleobases are particularly useful for increasing the binding affinity of the oligomeric compounds described herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 C and are presently preferred base substitutions, even more particularly when combined with 2'-O-methoxyethyl sugar modifications.

Another modification of the antisense oligonucleotides described herein involves chemically linking to the oligonucleotide one or more moieties or conjugates which enhance the activity, cellular distribution or cellular uptake of the oligonucleotide. The antisense oligonucleotides can include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes.

The method of the present invention employs use of vectors including a promoter and gene to be stably integrated into a genome. A "promoter" is a nucleic acid sequence that directs the binding of RNA polymerase and thereby promotes RNA synthesis. Promoter sequences include constitutive and inducible promoter sequences. In various aspects, the promoters can be naturally occurring promoters, hybrid promoters, or synthetic promoters. Hybrid promoters, which combine elements of more than one promoter, are also known in the art, and are useful in the present invention.

The vectors employed in the present invention may include a reporter gene/protein or reporter molecule to facilitate detecting the transcriptional activity of a gene, such as the telomerase gene. There are many genes and molecules that may be used in such a fashion. In various embodiments, the reporter protein may be luciferase (LUC), β-lactamase, chloramphenicol acetyltransferase (CAT), adenosine deaminase (ADA), aminoglycoside phosphotransferase (neo, G418), dihydrofolate reductase (DHFR), hygromycin-B-phosphotransferase (HPH), thymidine kinase (TK), β-galactosidase (β-gal), and xanthine guanine phophoribosyltransferase (XGPRT), an affinity or epitope tag, or a fluorescent protein. In exemplary embodiments, the reporter protein is GFP or eGFP. A number of additional fluorescent proteins are known in the art and suitable for use with the present invention, including but not limited to blue fluorescent proteins (e.g., EBFP, EBFP2, Azurite, mKalama1), cyan fluorescent proteins (e.g., ECFP, Cerulean, CyPet) and yellow fluorescent proteins (e.g., YFP, Citrine, Venus, YPet). The present invention may also employ affinity or epitope tags, such as poly-His, GST, HA, Flag, myc, CBP, CYD (covalent yet dissociable NorpD peptide), HPC (heavy chain of protein C) peptide tags, MBP, or other tag well known in the art.

A nucleic acid is "operably linked" when it is placed into a functional relationship with another nucleic acid sequence. For example, DNA for a presequence or secretory leader is operably linked to DNA encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used for expression, as will be appreciated by those in the art. Numerous types of appropriate expression vectors, and suitable regulatory sequences are known in the art for a variety of host cells.

In another aspect, the invention provides an isolated mammalian cell line characterized by genome including a modified chromosome containing a telomere seed sequence and an endonuclease cleavage site downstream of the telomere seed sequence, wherein conditional cleavage of at the cleavage site will allow de novo elongation of the seed sequence. The cells are preferably mammalian cells, including murine or human cells. In an illustrative example provided herein the modified chromosome is mouse chromosome 4.

In yet another aspect, the invention provides a kit which includes cells of the mammalian cell line of the invention along with reagents for culturing the cells. The kit may further include reagents for measuring de novo telomere addition.

The following example is provided to further illustrate the advantages and features of the present invention, but are not intended to limit the scope of the invention. While they are typical of those that might be used, other procedures, methodologies, or techniques known to those skilled in the art may alternatively be used.

EXAMPLE 1

Development of Mammalian De Novo Telomere Addition Assay

Long-term cell viability is critically dependent on maintenance of telomere length. In humans, syndromes of telomere shortening cause age-related degenerative diseases that are often fatal. At the cellular level, the loss of tissue renewal that contributes to these diseases is caused by cellular recognition of short telomeres inducing apoptosis or cellular senescence. On the other hand, cancer cells avoid cell death by increasing or maintaining telomere lengths.

Telomere shortening occurs during normal cell division because DNA replication fails to copy the very end of the chromosome. Telomerase adds telomere repeats onto chromosome ends to balance the shortening that occurs in every replication cycle. The delicate balance of shortening and lengthening is regulated by an intricate series of feedback mechanisms to establish a robust telomere length equilibrium. Elucidating the molecular interactions that regulate telomere elongation is essential to understand telomere function and how it is disrupted in disease.

To identify novel regulators of telomere elongation in a mammalian system, an in vivo telomere elongation assay was developed where telomerase repeat addition can be monitored over 48 hours. In this example, the successful development of a de novo telomere elongation assay in mouse cells is discussed that allows measurement of telomerase-dependent de novo telomere addition in one cell cycle.

Results

Generation of Cell Line to Assay De Novo Telomere Addition

To examine potential mammalian genes that regulate telomere length, an assay was developed that allows visualization of telomere addition in vivo, referred here as ADDIT (Addition of de novo initiated telomeres). In a chromosomally stable CASTEiJ mouse fibroblast cell line, chromosome 4 (chr4) was modified to generate an internal 480 bp telomere 'seed' sequence followed by a unique I-Sce1 endonuclease cut site (FIG. 1A). The length of seed sequence was based on an early study showing that 400 bp of telomere repeats can act as functional telomeres. Using Southern blot analysis, two independent HYG-positive clones were identified, clone 1L and 1M, with a single chr4 allele correctly modified (data not shown).

To examine telomerase-dependent elongation, this cell line was engineered to conditionally express telomerase. The parental CASTEiJ mouse fibroblast cells were mTR$^{-/-}$ and a retrovirus containing mTR and the green fluorescence protein (GFP) that can be removed by FLP/FRT recombination was introduced. Telomerase activity was not found in the parental mTR$^{-/-}$ cells but was present in GFP-positive transduced cells (data not shown).

To cut the endogenous chromosome 4 at the engineered I-Sce1 site in vivo, a HA epitope tagged I-Sce1 endonuclease driven by a tetracycline-inducible promoter was stably integrated and single clones isolated. A clone SL13 that expressed HA-I-Sce1 only in the presence of doxycycline was identified (data not shown). To compare telomere addition in cells with and without telomerase, the cells were transfected with a construct expressing the flp recombinase, and flow cytometry was used to sort GFP positive (with mTR) and GFP negative (without mTR) cells. mTR level was measured by quantitative RT-PCR and confirmed mTR was present in GFP-positive cells, but absent in GFP-negative cells (data not shown). These populations are referred to as mTR+ or mTR−, respectively.

Cleavage of chromosome 4 with I-Sce1 will expose a telomere seed and allow telomere addition by telomerase (data not shown). A time course of I-Sce1 induction showed that chromosome cutting occurred in vivo as early as 8 hours after doxycycline treatment (data not shown). As a control, the genomic DNA was digested in vitro with purified I-Sce1 endonuclease to compare the genomic cut site in vivo and in vitro on the Southern blot. Close to 10% I-Sce1 cutting after doxycycline induction was detected, which is similar to previously shown efficacy of I-Sce1 cleavage in vivo. While this efficiency of cutting is not quite as high as found in yeast, which has a smaller genome, it was concluded it might be sufficient to examine telomere elongation in mouse cells.

De Novo Telomere Addition Only in Telomerase Positive Cells

To compare telomere addition in cells with and without telomerase, Southern blot was performed with mTR− and mTR+ cells collected at several different time points after doxycycline induction.

Figure 2:
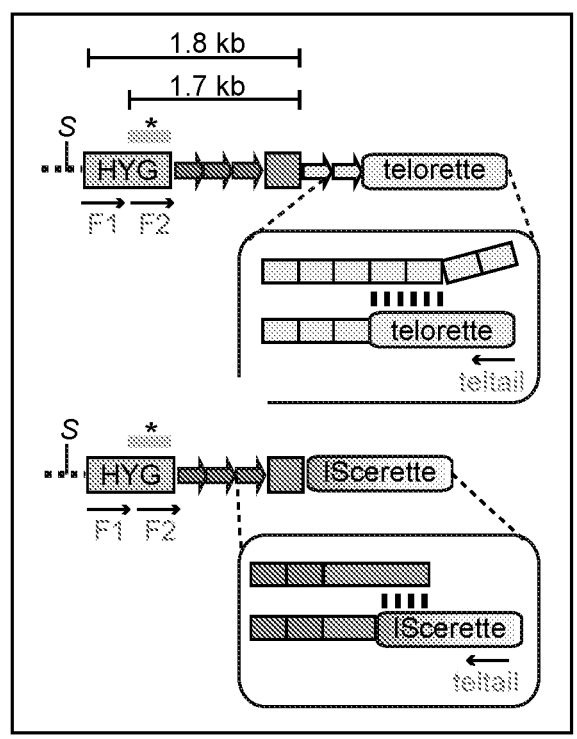
FIG. 2 is a pictorial representation showing that modified STELA PCR products indicate de novo telomere addition in mTR+ cells.

To better visualize the telomere addition on the I-Sce1 cut telomere seed, the single telomere length analysis (STELA) (Baird et al., 2004, Hum Mol Genet 13, 1515-1524), a PCR-based approach that can measure telomere lengths from individual chromosome ends was modified. The STELA assay employs annealing and ligation of a linker, 'telorette', with TTAGGG and a unique 20-nucleotide sequence to the G-rich 3' telomere overhang followed by PCR of the telomere from a 'teltail' primer and primer in the HYG sequence on the engineered chromosome (FIG. 2). The PCR product lengths will be proportional to the telomere lengths at the cleaved chr4 allele. As a control, to amplify the un-extended cut chromosome in vitro, a different linker, 'IScerette' was designed, which has a 4-nt homology to the 4-nt 3' overhang created by the I-Sce1 endonuclease at the cleavage site (FIG. 2). Genomic DNA digested with I-Sce1 endonuclease in vitro and ligated with the 'IScerette' linker and PCR amplified, generated the predicted length of STELA PCR product indicating that the IScerette linker efficiently ligated to the cleaved DNA (data not shown). This in vitro IScerette PCR product serves as a marker for the base line length of the cut, unextended telomere seed sequence.

STELA PCR products from genomic DNA of telomerase-positive cells (mTR+) treated with doxycycline were longer than the control IScerette products (data not shown), suggesting there was new telomeric sequence addition onto the seed sequence. In contrast, telomerase-negative cells (mTR−) treated with doxycycline resulted in STELA PCR product sizes only similar to and shorter than the base line, suggesting the longer products are dependent on telomerase activity.

Sequencing the De Novo Telomere Addition Products

To further verify the longer STELA PCR products represent de novo telomere addition, the PCR products were sequenced with Pacific Biosciences (PACBIO®) next generation sequencing technology. The PACBIO® platform produces longer reads and is less GC bias compared to other next generation sequencing platforms. While errors were present in the sequence as expected, the telomere repeats were easily recognizable. All of the reads from the PACBIO® were filtered and only those that had unique HYG sequence followed by telomere sequence and the 'teltail' primer sequence were examined. This assures that only full length of STELA PCR products were analyzed. The reads were then aligned at the junction between the HYG sequence and the telomere repeats. Wild-type TTAGGG repeats were colored orange and variant telomere repeats were colored in darker orange (FIG. 3A). Some of these variants arose due to errors in sequencing. An error rate similar to the published error rate of PACBIO® sequencing, 10-15% was observed. The errors were uniformly distributed over the reference sequence, dominated by point insertions and deletions, as expected for PACBIO® sequencing. There were three regions of divergent sequence in the original construct that are evident as darker orange stripes in the aligned reads (see for reference, in vitro IScelrette). These are small variation in TTAGGG sequence in the original SL13 clone and serve as useful internal reference points.

The PACBIO® sequence reads from the mTR+sample showed a heterogeneous population of telomere lengths and notably had a significant fraction of telomeric reads that contained the I-Sce1 recognition site followed by additional telomere sequences (FIGS. 3A and 3C). Telomerase has been shown to add telomere repeats onto primers (or sequences) that contain some non-telomeric sequence. The reads that are shorter than the reference sequence are presumably due to 5' end resection occurring in vivo at telomeres or internal deletions during sequencing.

In both the mTR– and the IScerette samples, there were few reads that appeared slightly longer than the initial input of telomere seed sequence (FIG. 3A). Careful examination of these sequences indicated that they did not contain telomere repeats that were added to the I-Sce1 site as were seen in the mTR+ samples. This suggests that these longer products that are present in both in vitro and in vivo experiments occurred through slippage during STELA PCR and/or the PacBio® sequencing. Because of this slippage, only those reads that contain telomere sequence past the I-Sce1 as de novo telomere elongation were defined.

Telomere elongation is regulated by two main processes of telomerase: 1) the processivity of the telomerase enzyme and 2) the recruitment of telomerase to the de novo end. Since the ADDIT assay measures addition of telomeres in only one cell cycle, the processivity of telomerase would regulate the length of de novo sequence added in one round of elongation. In contrast, the number of ends elongated will represent the probability of telomerase recruitment to an end in one cell cycle. The percentage of PacBio® reads with any de novo telomere sequence for each sample was measured, to address the probability of telomerase recruitment to the induced chr4 end. Notably, in the mTR+ cells, approximately 25% of the reads had telomere sequence after the I-Sce1 site indicative of de novo elongation (FIG. 2.3B). The presence of this longer class is consistent with the heterogeneous smear longer than the base line in the STELA PCR products (data not shown). Telomere lengths from mTR– sample were also heterogeneous; however, no addition of repeats beyond the I-Sce1 site was seen (FIGS. 3A and B), suggesting de novo telomere addition did not occur. As expected, sequence reads from the in vitro IScerette control sample were less heterogeneous and matched the reference sequence although some insertions and deletions, likely due to sequencing errors, were seen (FIG. 3A).

Figure 4A:
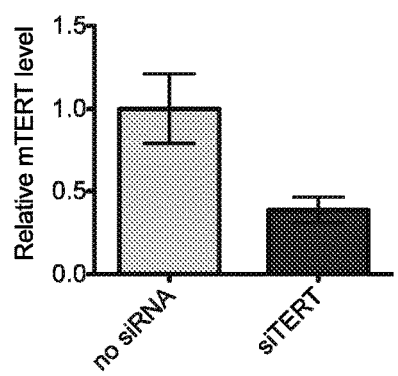
FIGS. 4A-4C are pictorial and graphical representations showing that de novo telomere addition is absent in siTERT-treated cells.
Figure 4B:
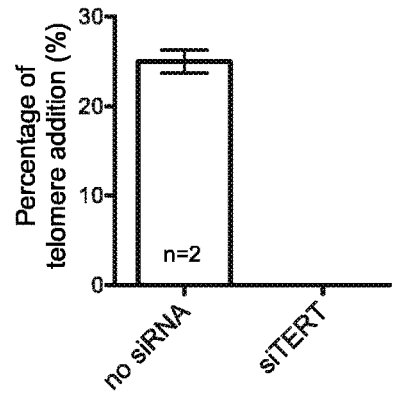
Figure 4C:
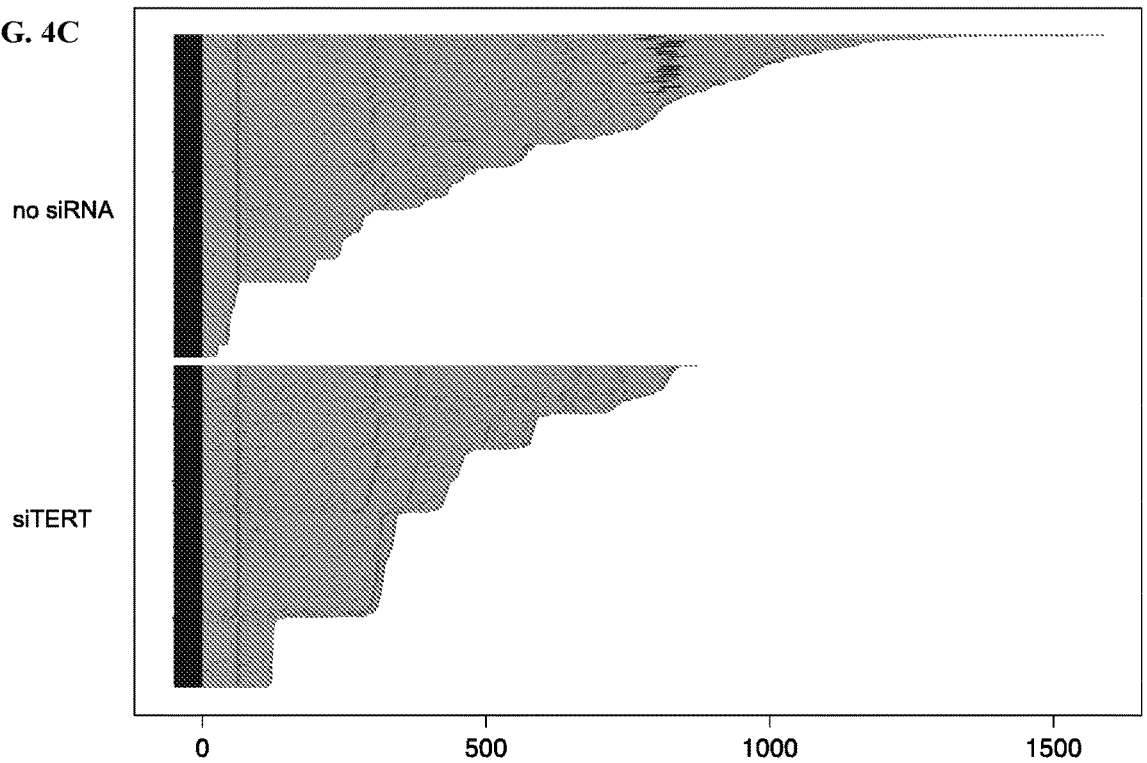

As an independent method to confirm that the de novo telomere addition is telomerase-dependent, cells were treated with siRNA against TERT (siTERT), the catalytic component of telomerase, to inhibit the telomerase activity and then performed the ADDIT assay. TERT RNA expression level was verified and was reduced more than 60% compared to the control by quantitative RT-PCR (FIG. 4A). As expected, none of the PacBio® reads from siTERT-treated sample showed de novo telomere addition (FIGS. 4B and 4C). Altogether, these results confirm the de novo telomere addition observed by the ADDIT assay is telomerase-dependent.

Classification of De Novo Telomere Addition

During the elongation cycle, telomerase uses the template region of the mTR to add telomere repeats. The telomerase RNA has a primer-alignment region adjacent to the template sequence that specifies the nucleotides added by the active site (FIG. 5A). The alignment region plays an important role in positioning the telomere substrate. For the mouse TR, there is a 2-nt alignment region, while the human RNA contains 5 nucleotides in the alignment region. Evaluation of the I-Sce1 cleavage site showed that it has some sequence similarity to a telomeric sequence and can base pair with the mTR primer-alignment region (FIG. 5A).

All of the reads in the mTR+ sample were classified into six different classes of telomere repeat addition (FIG. 5B). Each of these classes can be distinguished by the degree of 3' end resection of the I-Sce1 site and unique positioning of the 3' end with primer-alignment and template sequence in mTR. In 76 of the 697 PacBio® reads analyzed (11%), new telomeric repeats were directly added after the I-Sce1 3' overhang without any loss of nucleotides (Class 1, FIG. 5B).

The most common class of telomere addition (Class 3, 44%) had the most complementarity between the mTR primer and template sequence (AGGG). In this class, 4-bp overhang was lost as the telomeric repeats were added beyond the 3' G-rich sequence. The next most common telomere addition (Class 5, 24%) occurred by telomerase recognizing the G-rich sequence located upstream of the initial cut site, which also results in formation of three G:C base pairs. Interestingly, in Class 2, the 3' end resection positions the de novo 3' end within the alignment region of mTR and resulted in the incorporation of a C at the junction with the telomere repeats that is not in the I-Sce1 site nor the telomere sequence. This occasional incorporation of nucleotides that are normally in the alignment region as a template has also been found in telomerase RNA mutant in vitro. This incorporation of the templated C residue further supports the conclusion that telomere repeats are being added by telomerase activity in vivo.

Kinetics of De Novo Telomere Addition.

To measure how efficiently telomere addition occurs in vivo, cells were collected at different time points after doxycycline induction and performed the ADDIT assay. A high percentage of de novo telomere addition was observed 24 hours (hrs) post-doxycycline treatment but not in the early time points (FIG. 5). Given that telomere seed is exposed in vivo as early as 8 hrs after doxycycline induction (data not shown) and population doubling time of SL13 cells is 24 hrs, the short period of time of 8 to 16 hrs required to detect de novo telomere addition suggests the elongation occurred in one cell cycle.

Figure Legends

Figure 1B:
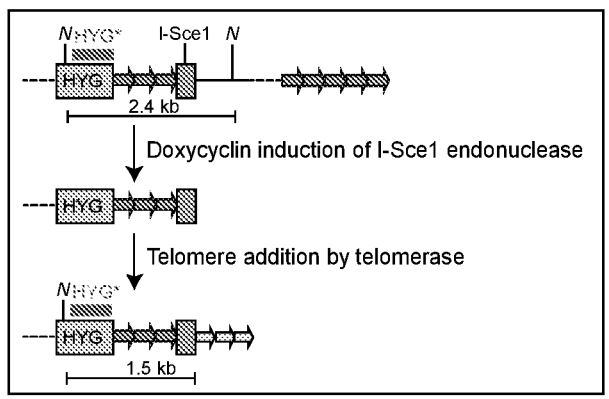

FIG. 1 pertains to generation of cell line to assay de novo telomere addition. (A) The chr4 subtelomeric targeting construct has two homology arms, hygromycin cassette (HYG), 480 bp telomere sequence (arrows) followed by I-Sce1 restriction site as well as the HSV-tk cassette. The predicted sizes of AflII-digested genomic DNA of wild-type mouse chr4 allele and correctly targeted allele are shown. A, AflII; B, BstBI; X, XhoI. (B) Schematic of the ADDIT assay. Doxycycline induction of I-Sce1 endonuclease exposes the telomere 'seed' sequence. New telomere repeats (lighter arrows) are added by telomerase. The predicted sizes of NcoI-digested genomic DNA of chr4 allele before and after I-Sce1 cutting are shown. N, NcoI.

FIG. 2 shows that modified STELA PCR products indicate de novo telomere addition in mTR+ cells. Representation of modified STELA, showing primers (arrows) and linkers either 'telorette' added to telomere or 'IScerette' added to cleaved I-Sce1 end. Telomeres were PCR amplified with a forward primer, either F1 or F2, and a reverse primer, teltail. Orange boxes represent telomere repeats and green box represents I-Sce1 restriction sequence. S, Sph1.

FIG. 3 shows that de novo telomere addition occurs only in telomerase-positive cells. (A) Analysis of PACBIO® circular consensus sequence (CCS) reads is shown. Reads were filtered for those that have both the unique HYG sequence followed by telomere sequence and also have the 'teltail' primer sequence, to assure only full length of STELA PCR products were analyzed. Wild-type telomere repeats are shown in orange, divergent telomeric sequence in darker orange and the I-SceI site is shown in green. X-axis indicates the length (bp) from the start of the telomere seed sequence. Maximum of 500 reads from each sample were shown for simplicity. (B) The percentage of PACBIO® CCS reads with de novo telomere repeats was calculated from each sample by using the following formula: 100%.times. (number of CCS reads with telomere repeats added beyond the I-Sce1 site)/(number of total CCS reads). n, number of independent samples analyzed. (C) The sequences of PACBIO® CCS reads boxed in A are shown.

FIG. 4 shows that de novo telomere addition is absent in siTERT-treated cells. (A) Relative expression levels of mTERT normalized to HPRT measured by quantitative RT-PCR. Error bars indicate the SEM from triplicates of SL13 untreated and treated with siTERT at final concentration 10 nM. (B) The percentage of PacBio® CCS reads with de novo telomere repeats was calculated from each sample by using the following formula: 100%×(number of CCS reads with telomere repeats added beyond the I-Sce1 site)/ (number of total CCS reads). n, number of independent samples analyzed. (C) PacBio® analysis of samples either treated with or without siTERT (maximum of 400 CCS reads shown for simplicity). X-axis indicates the length (bp) from the start of the telomere seed sequence. Note increased size length of seed sequence and two additional darker stripes that serve as internal reference points were detected from both samples indicating possible duplication of the telomere seed sequence from the original SL13 cell line.

FIG. 5A-5B shows the classification of de novo telomere addition. (A) The 42-nt unique sequence (the 5'-3' and 3'-5' sequences at lines 1-2) located immediately after telomere seed includes the 18-nt I-Sce1 recognition site (black box). I-Sce1 cut leaves a 3' 4-nt overhang. The sequences of the telomerase mTR template (underlined) and primer-alignment region (double underline) are shown. Potential Watson-Crick base-pairings indicated by vertical lines. Wobble pairing shown with dotted vertical lines. (B) Total n=697 of PACBIO® reads from wild-type sample (mTR+in FIG. 3A) were classified by where the telomere repeat sequences were added, and the percentage of reads followed in each class are shown. The different degree of 3' end resection of the I-Sce1 site and potential positioning with mTR primer region is shown along with a representative PACBIO® read of each class. The incorporation of a C in Class 2 is the first nucleotide in the boxed sequence. De novo added wild-type telomere repeats are boxed.

Figure 6A:
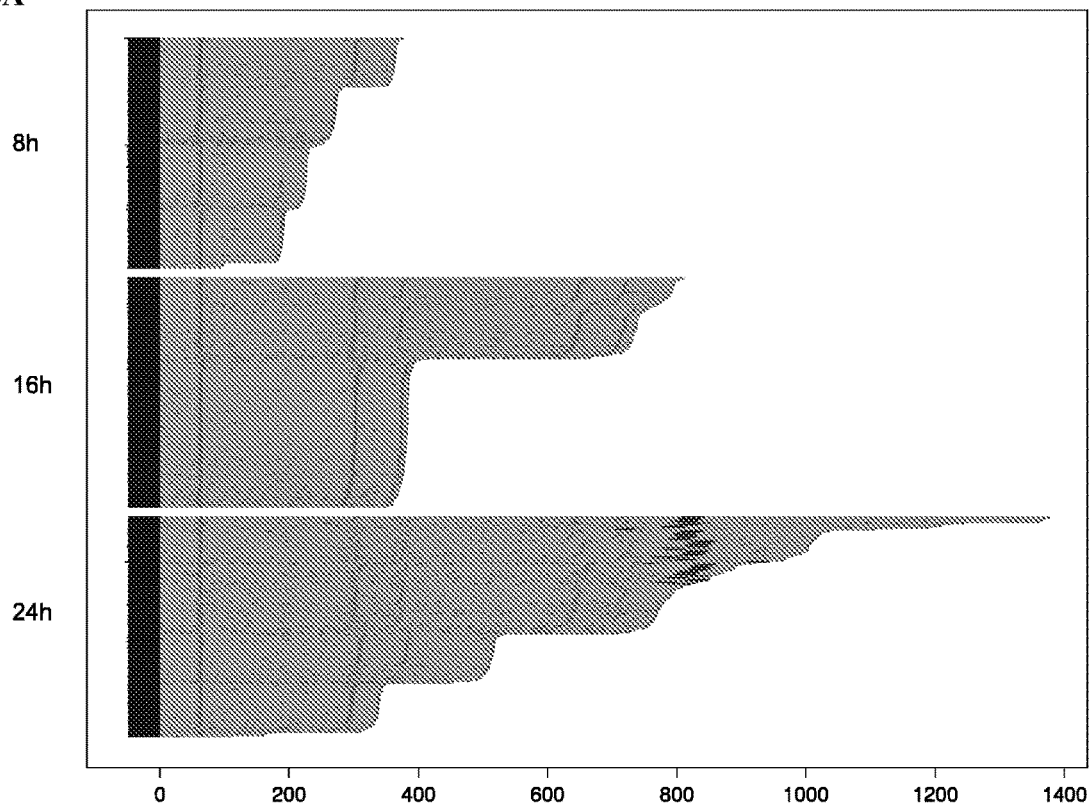
FIGS. 6A-6B are pictorial and graphical representations showing de novo telomere addition occurs as early as 24 hrs after seed sequence exposure.
Figure 6B:
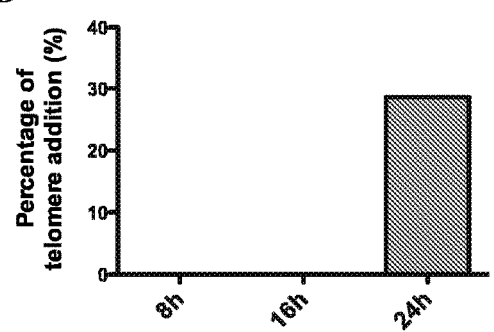

FIG. 6 shows that de novo telomere addition occurs as early as 24 hrs after seed sequence exposure. (A) PacBio® analysis of CCS reads from samples collected at different hours after doxycycline exposure is shown (maximum of 250 reads for simplicity). X-axis indicates the length (bp) from the start of the telomere seed sequence. Note increased size length of seed sequence and two additional darker stripes that serve as internal reference points indicating possible duplication of the telomere seed sequence from the original SL13 cell line. (B) The percentages of PacBio® CCS reads with de novo telomere repeats from A.

Figure 7:
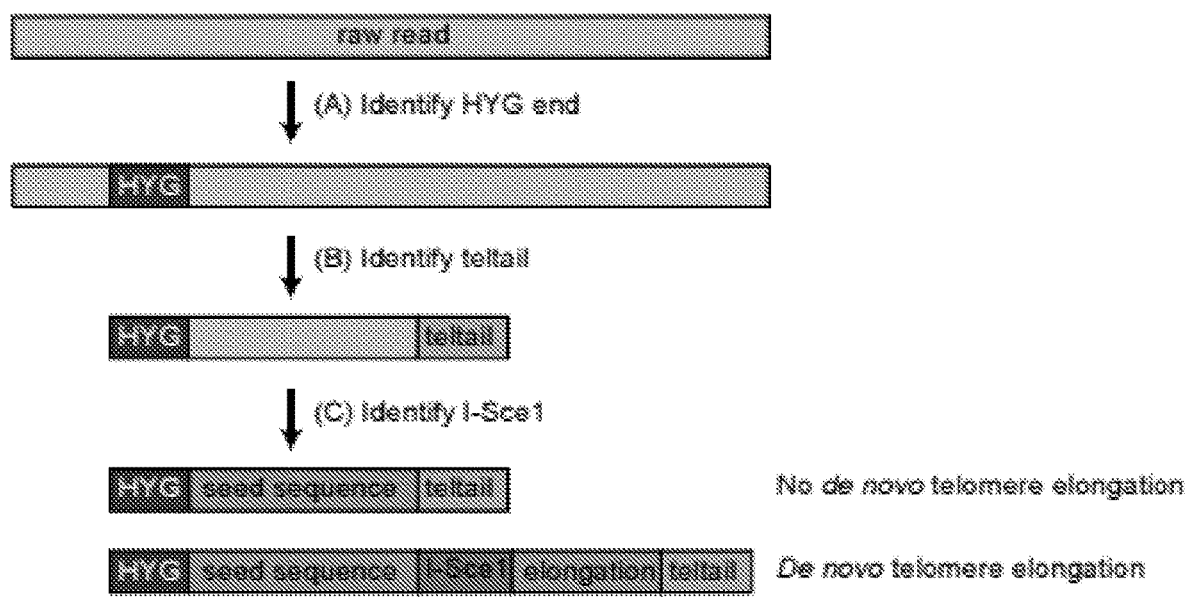
FIG. 7 is a flow diagram depicting the pipeline of PacBio® sequence read analysis.

FIG. 7 shows the pipeline of PacBio® sequence read analysis. (A) PacBio® sequencing reads were aligned to the last 50 bases of the hygromycin gene sequence (HYG) using the pairwiseAlignment function in the Biostrings™ package in Bioconductor™ (Pages H.) with parameters: local-global, mismatch penalty −3, match bonus 2, gapOpening −2, gapExtension −2. (B) Using the same parameters, the last X bp of the 3' ends of reads (where X is 1.5 times the maximum-length teltail sequence) to the teltail sequence were aligned. In multiplexed runs, all possible barcoded teltail sequences were aligned and only the best alignment considered, excluding reads that aligned equally well to multiple barcoded teltail sequences. Reads with a HYG alignment score greater than or equal to 60 and a teltail alignment score greater than or equal to 20 were kept for subsequent analysis. (C) Reads were then aligned by the sequence between the end of the HYG alignment and the start of the teltail alignment to the I-Sce1 sequence with parameters: local, mismatch penalty −3, match bonus 2, gapOpening −2, gapExtension −2. A score of 36 was sufficient to identify the I-Sce1 sequence. The parsed read set was manually curated to ensure that seed and elongation sequences contained telomeric repeats. Additional functions used in the pipeline were provided by the R packages parallelMap and stringr.

Discussion

In this example, successful development of the ADDIT assay that can identify novel mammalian genes required for telomerase-dependent telomere elongation by measuring de novo telomere addition at a single chromosome is discussed. It was verified that the telomere addition is telomerase-dependent and occurs in vivo over just one cell cycle. It takes roughly 6 to 8 weeks to observe bulk telomere length change in mammalian cells; however, by monitoring a single chromosome end, ADDIT assay can detect telomere changes less than a day. The very brief time required for the assay also allows the identification of essential genes that are difficult to probe for roles in telomere length regulation with the conventional method of long-term cell growth.

The ADDIT assay was designed in mouse CASTEiJ cells that have telomere length and distribution very similar to humans, in contrast to standard laboratory strains. This allows functional probing of telomeres in a setting similar to human telomere length regulation. The assay will provide insights into telomere length homeostasis and may allow identification of potential targets for future therapeutics.

Materials and Methods

Plasmid Construction

Chr4 Targeting Construct (p1SL25)

The chr4 subtelomeric targeting construct was made in multiple steps. The chr4 homology arms were amplified from BAC clone (#RP24-225H17) using the following primers: $1^{st}$ arm_F, $1^{st}$ arm_R, $2^{nd}$ arm_F and $2^{nd}$ arm_R. The telomere seed sequence was amplified from JHU821 plasmid (described in Morrish and Greider, 2009, *PLoS Genet* 5, e1000357) using primers pBlueSK_F and JHU821_SalI_R. HSV-tk was PCR amplified from plasmid GFAP-HSV-tk (pTGB008, Addgene #24703) using primers HSVtk_F and HSVtk_R. All fragment sequences were verified and cloned in pMSCV-HYG vector (p1SL25). p1SL25 construct was linearized with XhoI and NotI to yield a ~16 kb fragment, which was gel purified prior to transfection.

mTR/EGFP Retroviral Construct (p1SL8)

To generate a mTR-conditional cell line, mTR driven by its endogenous promoter was amplified from pMSCV-mTR-HYG plasmid using primers Hpa1FRT_mTR_F and mTR_EcoR1_R. EGFP with FRT site was amplified from plasmid pcDNA5/FRT/TO (Invitrogen) using primers EcoR1_EGFP_F and Cla1_FRT_EGFP_R. These two fragments were cloned in a retroviral vector pMSCV-HYG to generate p1SL8.

Dox-Inducible HA-I-Sce1 Construct (p1SL39)

To generate a Dox-inducible HA-I-Sce1 expression system, a lentiviral construct containing HA-I-Sce1 driven by a tetracycline-inducible promoter (pSL39) was generated by assembling four fragments using the GIBSON ASSEMBLY® cloning kit (NEB).

The selection marker GFP from the original Lenti-tet-ON plasmid (Holland et al., 2012, *Genes & Development* 26, 2684-2689) was replaced with red fluorescence protein (RFP). The four fragments are the following: (1) HA-I-Sce1 fragment amplified from pCBASce1 (Addgene #26477) using primers Isce1_F1 and Isce1_F2; (2) TetR fragment amplified from Lenti-tet-ON plasmid using primers rTetR_F2 and rTetR_R2; (3) RFP cassette amplified from dsRed-Express2 plasmid using primers dsRed-Express2_F3 and dsRed-Express2_R3_T; (4) vector fragment Lenti-tet-ON plasmid digested with AgeI and BsrGI. PCR products as well as the final constructs were all sequence verified.

Cell Culture and Treatments

Cell lines including 293T, 293FT, Pheonix, clone 1L and mTR$^{-/-}$ skin fibroblasts were grown in DMEM (Gibco) supplemented with 1% Penicillin/Streptomycin/Glutamine (PSG) and 10% heat inactivated FBS (Invitrogen). SL13 cells were grown in DMEM (Gibco) supplemented with 1% PSG and 10% Tet system approved FBS (Clontech, #631107).

Development of SL13 Cell Line

First, to generate the telomerase-conditional cell line, mTR$^{-/-}$ skin fibroblasts from CAST/EiJ mice (Morrish and Greider, 2009, *PLoS Genet* 5, e1000357) were transduced with the mTR/GFP retrovirus (p1SL8) (retrovirus transduction protocol described in more details below) and flow sorted for GFP-positive fluorescence. To modify the chr4 allele, GFP-positive cells were transfected with linearized chr4 targeting construct (p1SL25) using Xtreme 9™ (Roche). After 3 days of transfection, cells were selected for hygromycin resistance at final concentration of 500 μg/ml for 1 week followed by an additional 1 week of negative selection with glanciclovir at 35 μg/ml final concentration to select against Tk gene. The HYG$^R$GVC$^R$ cells were plated at a very low density and grown for approximately 2 weeks until clonal populations were visible. Clonal populations were isolated with cloning cylinders (Sigma, #C1059) and screened for correct integration by Southern analysis. To integrate the doxycycline-inducible HA-I-Sce1 expression system, clone 1L was transduced with lentivirus p1SL39. Later RFP-positive cells were flow sorted in 96-well plate as single clones. To induce I-Sce1 expression, doxycycline at final concentration of 2 μg/ml was added to cells. Typically cells were collected post 48 hours of doxcycline treatment. Clones were screened for doxycycline-dependent HA-I-Sce1 expression by Western blot. To collect telomerase-negative cells, SL13 cells were transfected with a plasmid (pPGKFL-PobpA, Addgene #13793) expressing flp, then approximately 10 days later GFP+ and GFP− cells were flow sorted.

Retrovirus Packaging and Transduction

To generate the telomerase-conditional cell line, mTR$^{-/-}$ skin fibroblasts from CAST/EiJ mice (Morrish and Greider, 2009, *PLoS Genet* 5, e1000357) were transduced with the mTR/GFP retrovirus (p1SL8). In brief, 2×10$^6$ Pheonix cells were plated onto 10-cm polystyrend plates (BD Falcon) in 10 ml complete medium (DMEM (Gibco), 10% MS (Gibco), 1× PSG (Gibco)) and allowed to double overnight. The following day, cells were transfected with 2 μg of p1SL8 plasmid. Transfection was performed with FuGENE-6 (Promega) and Opti-MEM serum-free medium (Gibco). The next day following transfection, cells were fed with 3-4 ml of fresh media and incubated at 32° C. Viral supernatant was collected at 48 and 72 hrs post-transfection, and filtered through a 0.45 μm CN filter (Thermo Scientific) to eliminate any remaining non-viral debris. The viral supernatant was immediately used or stored at 4° C. For titering, 293FT cells were seeded in complete medium in 6-well plates at 10$^5$ cells/well and allowed to double overnight. The following day, polybrene-treated cells (8 μg/ml, Sigma) were infected with 1 and 2 μl as well as mock-infected controls with 1× PBS, and incubated overnight at 37° C., 5% CO$_2$. The following morning, the medium was changed to eliminate the polybrene, which is toxic to cells. Cells were allowed to divide for an additional 36-48 hours and the percentage of GFP-positive cells determined by flow cytometry, a total of 48-60 hours post-infection. The viral titer (T.U./μl) was calculated using the following formula: $\{2\times10^5 \text{ cells}\times(\% \text{ GFP-positive cells}-\% \text{ GFP-positive mock-infected cells})\}/1$ or 2 μl. To infect mTR/GFP retrovirus (p1SL8) with MOI<1, 1×10$^6$ mTR$^{-/-}$ skin fibroblasts were incubated with 3.5 ml of 48 hrs viral supernatant as well as final concentration 8 ug/ml polybrene at 32° C. After 6 hrs, supernatant was removed and refreshed with complete medium. 24 hrs after the first infection, the viral infection was repeated with the 72 hrs viral supernatant.

Lentivirus Packaging and Transduction

To generate a doxycycline-inducible HA-I-Sce1 expression system, lentivirus p1SL39 was first made. Briefly, 15-cm polystyrend plates (BD Falcon) were coated with 100 μg/ml sterile poly-D lysine and 6-8×10$^6$ 293FT cells were plated in complete medium (DMEM (Gibco), 10% FBS (Gibco), 1× PSG (Gibco)) and allowed to double overnight. The following day, the medium was changed to DMEM, 1% FBS and cells were co-transfected with 3 plasmids: p1SL39 (containing the HA tagged I-Sce1), pCMVΔ8.91 (containing the gag and pot lentiviral genes), and pVSV.G (containing the env lentiviral gene). Transfections were performed with Lipofectamine 2000™ (Invitrogen) and Opti-MEM™ serum-free medium (Gibco). After 48 hrs, the supernatant was collected, centrifuged for 5 minutes at 1000 rpm to get rid of large cell debris, and filtered through a 0.45 μm CN filter (Thermo Scientific) to eliminate any remaining non-viral debris. Aliquots of filtered supernatant were frozen at −80° C. or used immediately. To transduce p1SL39 lentivirus, clone 1L cells were seeded in complete medium in 6-well plates at 10$^5$ cells/well and allowed to double overnight. The following day, polybrene-treated cells (8 μg/ml, Sigma) were infected with p1SL39 lentivirus and incubated overnight at 37° C., 5% CO$_2$. The following morning, medium was changed to eliminate the polybrene and refreshed with complete medium. To estimate the efficiency of transduction, RFP intensity was measured by flow cytometry after 48 hrs.

Quantitative RT-PCR

To measure mTR levels, total RNA (1 μg) from wild-type, GFP+ and GFP− cells was reverse transcribed using random hexamers and Superscript III™ reverse transcriptase (Invitrogen), following the manufacturer's instructions. Quantitative RT-PCR was performed using a CFX96 thermocycler (Bio-Rad). Each quantitative RT-PCR reaction contained 1× SYBR Green Supermix and 5 μM of each primer. Roughly, 5 ng cDNA were amplified per reaction. The expression in each sample was normalized to HPRT. The cycling conditions for mTR were as follow: 5 minutes at 95° C.; 15 seconds at 95° C., 30 seconds at 68° C., 45 seconds at 72° C., 10 seconds at 82° C. (35 cycles); 3 minutes at 72° C. For each cycle, fluorescence readings were performed at the 82° C. step, to avoid generation of primer dimers. Primers used were the following: RT_mTR_F, RT_mTR_R, HPRT_F and HPRT_R. Triplicates were run for each sample and the normalized average was reported.

Telomeric Repeat Addition Protocol (TRAP)

Telomerase activity was measured using the telomeric repeat amplification protocol (TRAP), a 2-step PCR-based assay. Briefly, cells were spun down and washed, and cell extracts were generated by resuspending the pellets in 1× CHAPS lysis buffer (10 mM Tris-HCl pH 7.5, 1 mM $MgCl_2$, 1 mM EGTA pH 8.0, 0.1 mM benzamidine, 5 mM β-mercaptoethanol (BME), 0.5% CHAPS, 10% glycerol). After a 30 minute incubation on ice, cells were spun down for 20 minutes at 14,000 rpm at 4° C. The supernatant was collected and half of it was treated with 2 µg RNase A, incubated for 10 minutes at 65° C., then chilled on ice. In step 1, RNase A-treated and untreated lysates were incubated with 1× TRAP reaction buffer (200 mM Tris-HCl pH 8.3, 15 mM $MgCl_2$, 630 mM KCl, 0.5% Tween-20, 10 mM EGTA, pH 8.0), 0.1 mM dNTPs, and 34 µM TS primer for 1 hour at 30° C. For the second TRAP step, 2 µl of the extension products in step 1 were added to 48 µl of a master mix containing 1× Taq buffer (Denville), 0.1 mM dNTPs (TaKaRa), 2 U Taq polymerase (Denville), 20 µM end-labeled TS primer (4 µCi γ-$^{32}$P-ATP, 1× PNK forward buffer (Invitrogen), 20 µM TS primer, 1 U T4 PNK (Invitrogen); 30 minutes at 37° C., 15 minutes at 65° C.) and primer mix (8.5 µM reverse primer, 17 µM internal control reverse primer K1, $10^{-12}$ µM internal control template TSK1). A 2-step PCR amplification protocol was used (94° C.×10 min; 30 cycles of 94° C.×30s, 59° C.×30 sec). PCR products were mixed with 1× GelPilot DNA loading dye (QIAGEN) and separated on a 10% non-denaturing polyacrylamide gel (1× TBE, 10% acrylamide/bis solution (19:1) (BioRad), 2% glycerol, 0.144% ammonium persulfate (Sigma), 0.04% N,N,N',N'-Tetramethylethylenediamine (Sigma)) by running the gel for 90 minutes at ≤20 W and drying at 80° C. for 1 hour. Due to the repetitive nature of the telomeric sequence, the resulting PCR products consist of fragments that are separated by six basepairs. The dried gel was exposed on a phosphorimager screen and scanned on a Storm 860™ imager (GE Healthcare).

Southern Blot Analysis

To screen for clones with correct modification at chr4 subtelomeric allele, genomic DNA was extracted from clones using the Puregene Core Kit A™ (Qiagen). AflII-digested genomic DNA was resolved by 0.7% Tris-acetate-EDTA (TAE) agarose gel electrophoresis. Following denaturation (0.5 M NaOH/1.5 M NaCl) and neutralization (1.5 M NaCl/0.5 M Tris-HCL pH 7.4), the DNA was transferred in 20× SSC to a Nylon Membrane (Amersham Hybond N+) by weighting method overnight and cross-linked with UV Stratalinker™ (Stratagene). Pre-hybridization was done at 42° C. for 2 hours in prehybridization buffer (50% Formamide/6× SSC/1% SDS/5× Dendart/sperm DNA) freshly made. A radioactive chr4 probe was made by random-prime labeling using Prime-It II™ (Stratagene) with a slight modification. Briefly, 25 ng of a 1.2 kb chr4 homology arm 2 containing probe, acquired from XcmI digestion of p1SL13-7 plasmid or 1 KB Plus DNA ladder (Invitrogen) was labeled using 33 µM of dATP, dTTP, 50 µCi of α-32P dCTP (3000 Ci/mmol) and 50 µCi α-32P dGTP (3000 Ci/mmol). Unincorporated nucleotides were removed using a G50 column (GE Healthcare). Labeled probe was counted and $10^6$ counts/ml (chr4 probe) or $10^4$ counts/ml (ladder) was denatured at 100° C. for 5 minutes and added to the pre-hybridization solution and hybridized overnight at 42° C. Membranes were washed 3× 15 minutes each in 6× SSC and 1% SDS at 65° C., and 3× 15 minutes each in 1× SSC and 1% SDS at 65° C. and exposed to a phosphorimager screen and detected on a Fuji phosphorimager. To examine the HYG-specific bands, the blot was stripped by incubating with 0.4M NaOH at 45° C. for 30 minutes followed by incubation in 0.1XSSC/0.1% SDS/0.2M Tris-HCl pH 7.5 at room-temperature for 15 minutes. The blot was prehybridized and re-probed with random primed α-32P-labeled HYG probe. HYG probe fragment was made by using the following primers: HYGprobe_F and HYGprobe_R. To examine the in vivo chr4 cleavage, genomic DNA extracted from SL13 cells treated with doxycycline for various time points were digested with NcoI restriction enzyme (NEB) and further analyzed by Southern as described with a random primed α-32P-labeled HYG probe.

Western Blot Analysis and Antibodies

To detect HA-tagged I-Sce1, 1× lysis buffer made of final concentration of 1× RIPA (Cell Signaling, #98016S), 1× protease inhibitor cocktail (Roche) was added directly to cells on the dish after washing with 1× PBS. Protein concentration was measured with a BCA protein assay kit (Thermo, #23227). Typically 10 µg of protein from each sample was applied to SDS-PAGE gels (Biorad, #456-1084) and transferred to nitrocellulose membranes in transfer buffer. After blocking with the Odyssey™ blocking buffer (LI-COR, #927-40000) for 1 hour at room temperature (RT), membranes were incubated at 4° C. overnight with primary antibodies: anti-HA (Santa Cruz, #sc-7392) and anti-Actin (Santa Cruz, #sc-1616). After incubation with secondary antibodies conjugated to near-infrared dyes (IRDye® 680 anti-goat, 800 anti-mouse, LI-COR), blots were scanned on a two-channel near-infrared Odyssey™ scanner (LI-COR).

Modified Single Telomere Length Analysis (STELA) for chr4

The original STELA protocol used for human cells (Baird et al., 2004, *Hum Mol Genet* 13, 1515-1524) was modified to measure telomere lengths on the de novo end of chr4 in SL13 cells. Briefly, genomic DNA was extracted using Puregene Core Kit A ™ (Qiagen). 4 µg of genomic DNA was digested with SphI (NEB) and later diluted to 10 ng/µl in water. For the in vitro IScerette sample, genomic DNA was digested with SphI and I-SceI (NEB) prior to ligation. The ligation was carried out at 35° C. for at least 12 hrs in a volume of 10 µl containing 10 ng of digested genomic DNA, 0.9 µM of telorette linkers (mixture of telorette 1 to 6) or IScerette linker and 0.5 U of T4 DNA ligase (NEB) in 1× T4 ligation buffer. Multiple PCRs (typically 24 or 32 reactions per sample) were carried out for each test DNA in volumes of 25 µl containing 1 ng of ligated DNA, 0.2 µM HYG-specific and teltail primers, 1× Fail Safe™ PCR buffer H (Epicentre FSP995H), 1 U of Fail Safe™ Enzyme Mix (Epicentre FS99100). The PCR conditions were the following: 94° C. for 15 sec, 25 cycles of 95° C. for 15 sec, 58° C. for 20 sec and 68° C. for 4 min, followed by 68° C. for 10 min. The PCR reactions were pooled for each sample and purified using magnetic beads (Agencourt AMPure XP™, Beckman Coulter). The concentration was measured and an equal amount of fraction from each sample was analyzed by Southern blot using a HYG probe.

siRNA-Mediated Knockdown of TERT

ON-TARGET™ siRNA SMART pools from GE Healthcare were used: mouse TERT (L-048320-01-0005). SL13 cells were subject to siRNA transfection using Pepmute™ protocol (SignaGen Laboratories, #SL100566) at a final concentration of 10 nM. The efficiency of knockdown was assessed by quantitative RT-PCR.

PacBio® Sequence Analysis

A pipeline in R (FIG. 7) was created that analyzes Pacific Biosciences sequencing data generated from modified STELA. First, reads were aligned to the last 50 bases of the HYG sequence using the pairwiseAlignment function in the Biostrings™ package in Bioconductor (Pages H.) (A), with parameters: local-global, mismatch penalty −3, match bonus 2, gapOpening −2, gapExtension −2. Using the same parameters, the last X bp of the 3' ends of reads were aligned (where X is 1.5 times the maximum-length Teltail sequence) to the Teltail sequence (B). In multiplexed runs, all possible barcoded Teltail sequences were aligned and only the best alignment considered, excluding reads that aligned equally well to multiple barcoded Teltail sequences. Reads with a HYG alignment score greater than or equal to 60 and a Teltail alignment score greater than or equal to 20 were kept for subsequent analysis. The sequence was then aligned between the end of the HYG alignment and the start of the Teltail alignment to the I-Sce1 sequence (C) with parameters: local, mismatch penalty −3, match bonus 2, gapOpening −2, gapExtension −2. A score of 36 was considered sufficient to identify an I-Sce-1 sequence. The parsed read set was manually curated to ensure that seed and elongation sequences contained telomeric repeats. Additional functions used in the pipeline were provided by the R packages parallelMap and stringr. The percentage of PacBio® CCS reads with de novo telomere repeats are calculated from each sample by using the following formula: 100%×{(number of CCS reads with telomere repeats added beyond the I-Sce1 site)/(number of total CCS reads)}.

TABLE 1

| Primer list | |
|---|---|
| To clone chr4 targeting construct (p1SL25) | |
| 1st arm F | GGCCTCGAGATATCTTCTGCT (SEQ ID NO: 52) |
| 1st arm R | GCCGTTAACAGAGGAACCAAG (SEQ ID NO: 53) |
| 2nd arm F | ATACGACTCACTATAGGGCGAATTG (SEQ ID NO: 54) |
| 2nd arm R | GTCCAGCATAAAGGCAAATGTGGC (SEQ ID NO: 55) |
| pBlueSK_F | GCCGCGTCGACATTAACCCTCACTAAAGGGAAC AAA (SEQ ID NO: 56) |
| JHU821 SaiI R | ATACGACTCACTATAGGGCGAATTG (SEQ ID NO: 57) |
| HSVtk F | GGCTTAATTAATAGAGGATCGATCTTGGTGGCG TGAAACTCCCGCACC (SEQ ID NO: 58) |
| HSVtk R | CTGGCGGCCGCTCCCGCGGAAACTCGGCCGTGG TGACCAATACAAAA (SEQ ID NO: 59) |
| To clone mTR/EGFP retroviral construct (p1SL8) | |
| HpaI FRT_mTR_F | GCCGTTAACGAAGTTCCTATTCTCTAGAAAGTA TAGGAACTTCGCGCCTGCCTTCGTCAAATTCT G (SEQ ID NO: 60) |
| mTR EcoR1 R | GCCGAATTCCGGATCTACGCCTGTAGTCCTCCC (SEQ ID NO: 61) |
| EcoR1 EGFP F | GGGCCCGCGAATTCTCGTAATAGTAATCAATTA C (SEQ ID NO: 62) |
| ClaI FRT EGFP R | CGCCCCATCGATGAAGTTCCTATACTTTCTAGA G (SEQ ID NO: 63) |

TABLE 1-continued

| Primer list | |
|---|---|
| To clone Dox-inducible HA-I-Sce1 construct (p1SL39) | |
| Isce1 F1 | CAAATTACAAAAATTCAAAATTTTATCGATATC CGCCGCCACTATGGGATC (SEQ ID NO: 64) |
| Isce1 R1 | GGAACTCCCAAGCTTATCGATTCGATCGACTTA TTATTTCAGG (SEQ ID NO: 65) |
| rTetR F2 | CCTGAAATAATAAGTCGATCGAATCGATAAGCT TGGGAGTTCC (SEQ ID NO: 66) |
| rTetR R2 | GACGTTCTCAGTGCTATCCATGGTTGTGGCCAT ATTATCATCG (SEQ ID NO: 67) |
| dsRed-Express2_F3 | CGATGATAATATGGCCACAACCATGGATAGCAC TGAGAACGTC (SEQ ID NO: 68) |
| dsRed-Express2_R3_T | CGACGCGGCCGCTTTACTTCTACTGGAACAGGT GGTG (SEQ ID NO: 69) |
| Quantitative RT-PCR | |
| HPRT F | TGATCAGTCAACGGGGGACA (SEQ ID NO: 70) |
| HPRT R | TTCGAGAGGTCCTTTTCACCA (SEQ ID NO: 71) |
| RT_mTR_F | TGTGGGTTCTGGTCTTTTGTTCTCCG (SEQ ID NO: 72) |
| RT_mTR_R | GTTTTTGAGGCTCGGGAACGCG (SEQ ID NO: 73) |
| TRAP | |
| TS primer | AATCCGTCGAGCAGAGTT (SEQ ID NO: 74) |
| reverse primer | CCCTTACCCTTACCCTTACCCTTA (SEQ ID NO: 75) |
| K1 primer | ATCGCTTCTCGGCCTTTT (SEQ ID NO: 76) |
| TSK primer | AATCCGTCGAGCAGAGTTAAAAGGCCGAGAAGC GAT (SEQ ID NO: 77) |
| HYG probe | |
| HYGprobe_F | ATGAAAAAGCCTGAACTCACCGCGACGTCT (SEQ ID NO: 78) |
| HYGprobe_R | GTGCTGGGGCGTCGGTTTCCACTA (SEQ ID NO: 79) |
| Modified STELA for chr4 | |
| Telorette 1 | TGCTCCGTGCATCTGGCATCCCCTAAC (SEQ ID NO: 80) |
| Telorette 2 | TGCTCCGTGCATCTGGCATCTAACCCT (SEQ ID NO: 81) |
| Telorette 3 | TGCTCCGTGCATCTGGCATCCCTAACC (SEQ ID NO: 82) |
| Telorette 4 | TGCTCCGTGCATCTGGCATCCTAACCC (SEQ ID NO: 83) |
| Telorette 5 | TGCTCCGTGCATCTGGCATCAACCCTA (SEQ ID NO: 84) |
| Telorette 6 | TGCTCCGTGCATCTGGCATCACCCTAA (SEQ ID NO: 85) |

TABLE 1-continued

Primer list

| | |
|---|---|
| Iscerette | TGCTCCGTGCATCTGGCATCTTAT (SEQ ID NO: 86) |
| HYG-specific F1 | CTGAACTCACCGCGACGTCTGT (SEQ ID NO: 87) |
| HYG-specific F2 | AGGAGGGCGTGGATATGTCCTGCGG (SEQ ID NO: 88) |
| Teltail | TGCTCCGTGCATCTGGCATC (SEQ ID NO: 89) |

EXAMPLE 2

Role of ATM Kinase in Telomere Elongation

The ATM and ATR kinase-dependent DNA damage response pathways are activated in primary human cells when telomeres are critically short. Induction of telomere dysfunction through a different mechanism, the removal of shelterin components, also activates ATM or ATR-dependent signaling. Which pathway is activated is dependent on which shelterin component is removed. Deletion of TRF1 (telomeric-repeat-binding factor 1) activates the ATM pathway while removal of POT1 primarily activates the ATR pathway.

While there has been significant progress and ongoing studies to understand the role of ATM and ATR in telomere dysfunction, less is known about the role of these kinases in normal telomere elongation, when telomeres are not critically short. A role for ATM in telomere length maintenance was first evident when the ATM gene was cloned and shown to be the homolog of the Tel1 gene in yeast. Loss of Tel1$^{ATM}$ function leads to short telomeres. Interestingly, while deletion of the related kinase Mec1$^{ATR}$ does not itself cause telomeres shortening, the double mutant of Tel1$^{ATM}$ Mec1$^{ATR}$ shows further shortening not seen in Tel1$^{ATM}$ mutant alone. This implies that Mec1$^{ATR}$ may partially compensate for the loss of Tel1$^{ATM}$.

The role of ATM in regulating telomere elongation in mammalian cells has been more controversial than in yeast. In human cells, a prominent, early paper suggested that ATM plays no role in human telomere maintenance. However other reports suggested cells might have shorter telomeres in the absence of ATM. The different methods for measuring telomeres and the small number of samples analyzed left this unresolved. Mouse studies on ATM and telomere elongation have also failed to find a definitive role for ATM. To detect telomere shortening in the absence of telomerase, it requires four to six generations of interbreeding telomerase null mice. Two groups showed that first generation ATM null mice do not have short telomeres. Progressive breeding of ATM$^{+/-}$ heterozygotes did not show telomere shortening. Since ATM$^{-/-}$ mice are sterile, it is not possible to interbreed them to examine telomere length over many generations. Thus the failure to see short telomeres in these mice might be simply due to the limitations of breeding. In addition, as discussed below, ATM and ATR play partially overlapping roles in several species, thus to see major changes in telomere length in mice may require reduction in both pathways.

Given the conserved role of ATM in telomere length regulation in *S. cerevisiae, S. pombe* and *Arabidopsis*, the role of ATM kinase in telomere elongation in mammalian cells was examined. To avoid the issues of breeding ATM$^{-/-}$ mice and missing small effects of telomere length changes on long telomeres, the ADDIT assay (described in Example 1) was used so that telomerase repeat addition can be monitored over one cell cycle. Using this assay, it was demonstrated that ATM kinase pathway regulates telomerase-mediated telomere elongation. This highlights the conserved nature of the pathways that regulate telomere length across species and suggests novel approaches to manipulating telomere length.

Results

ATM Kinase is Essential for De Novo Telomere Addition

Having established the robust ADDIT assay that can measure telomere elongation over one cell cycle, it was desired to examine whether the ATM kinase activity is required for telomere elongation. Two different methods were used to inhibit ATM: the ATM specific inhibitor KU55933 and siRNA knockdown. To confirm the inhibition of ATM kinase activity, the phosphorylation level of ATM substrate Kap1 as well as ATR kinase substrate Chk1 was examined by western blot. Cultured cells were pretreated with KU55933, siATM or DMSO control and later exposed to a DNA damaging reagent Camptothecin (CPT). Western blot analysis with antibodies to the phosphorylated Kap1-S824 and Chk1-S345 indicated that KU55933 and siATM blocked Kap1 phosphorylation but not Chk1 phosphorylation (data not shown). This indicated that both KU55933 and siATM specifically inhibited the ATM kinase-dependent signaling pathway, while the ATR pathway was not affected.

Telomere elongation was measured by the ADDIT assay in cells treated for 48 hrs with doxycycline to induce I-Scel in the presence or absence of KU55933 or siATM.

PACBIO® sequencing of the STELA products indicated that addition of de novo telomere repeats beyond the I-Scel site was significantly reduced when ATM was inhibited or knocked down (FIGS. 8A and 8B). Cells treated with the KU55933 had fewer and significantly shorter elongation products while cells treated with siATM showed no telomere elongation (FIGS. 8A and 8C). These results indicated that ATM activity is required for telomerase-mediated de novo telomere repeat addition.

Inhibition of ATM Kinase Prevents Telomere Elongation by Telomere Overexpression To examine the role of ATM in telomere elongation by an independent method, telomerase was overexpressed in the cell line, in the presence of ATM inhibition. It has been shown that overexpressing telomerase elongates telomere lengths in human cells. Cells were treated with KU55933 and then transduced with a lentivirus expressing both mTR and mTERT and grown for 2 or 5 days in culture and telomere lengths were assayed by Southern blot. Telomere lengths in cells overexpressing telomerase were rapidly elongated in just 5 days (data not shown). However, treatment with KU55933 significantly blocked the telomere elongation. Significant blocking of elongation in the siATM treated cells was not seen even though the expression levels of ATM protein and ATM-dependent phosphorylation of KAP1 were decreased. This is likely due to the transient effect of knockdown by siRNA, which may explain why telomere shortening has not previously been reported in siRNA experiments with ATM. In addition, as discussed below, when cells are grown for several days, ATR may also compensate for the loss of ATM. The results from the ADDIT assay showing abrogation of telomere elongation and the Southern data collectively indicate that ATM kinase is required for telomere elongation by telomerase.

Inhibition of ATM Kinase Shortens Telomere Length

Given that ATM inhibitor KU55933 treatment prevents telomere elongation by telomerase overexpression, whether KU55933 treatment shortens telomere lengths in continuously growing cells was tested. SL13 cells were grown in the presence of KU55933 and measured the telomere lengths at various population doublings (PDs). Telomeres of KU55933-treated cells gradually shortened with increasing cell PDs (FIG. 9B). Densitometry of the Southern lanes showed shorter telomeres in the later PDs (FIG. 9B, pixel position 2). The distinct non-telomeric bands served as useful loading controls, confirming all lanes were equally loaded (FIG. 9B, pixel position 1 and 3). To examine whether telomere shortening in ATM inhibition also occurs in human cells, human HCT116 cells were treated with KU55933 drug. Consistent with the observations from mouse cells, telomere lengths of HCT116 shortened significantly in the presence of KU55933 with increasing cell PDs. Altogether these results further indicate that ATM kinase is a positive regulator of telomere elongation in both mouse and human cells.

Activation of ATM kinase Pathway Elongates Telomere Lengths

Since inhibition of ATM kinase gradually shortened telomere lengths, whether activation of ATM kinase pathway would result in telomere elongation was investigated. A previous study showed that the ATM kinase pathway is activated following inhibition of poly (ADP-ribose) polymerase 1 (PARP1), an essential enzyme involved in DNA repair pathway. To examine activation of ATM kinase pathway in response to PARP1 inhibition in our cells, the phosphorylation levels of KAP1, a known target of ATM kinase, in response to PARP1 specific inhibitor, Olaparib was measured. Cells treated with Olaparib indeed had a 5-fold increased level of Kap1 phosphorylation, compared to DMSO-treated control cells. Although the level of KAP1 phosphorylation was not as robust as cells treated with DNA damaging reagent CPT, some induction was seen. To test whether this PARP inhibitor-induced ATM activation would stimulate telomere elongation, SL13 cells were grown in the presence of Olaparib and collected at various PDs and telomere length was measured by Southern blot analysis. Strikingly, telomere lengths gradually increased after 25 PDs in the presence of Olaparib and were further elongated in later PDs. To verify whether telomere elongation in response to PARP inhibition is through activation of ATM kinase pathway, testing whether blocking ATM would block the elongation effect of the PARP inhibitors was desired. Unfortunately, similar to other studies, cells were too sensitive to combination of KU55933 and Olaparib treatment for long-term cell growth. As such, the ADDIT assay was used to examine de novo telomere elongation in cells treated with either DMSO, KU55933, Olaparib or both drugs. Cells treated with KU55933 alone had less de novo telomere addition compared to DMSO control consistent with previous results. In contrast, cells treated with Olaparib had significantly higher percentage of de novo telomere addition. In the cells treated with both Olaparib and KU55933, the percentage of reads with telomere elongation was reduced from 22.4% to 18.1%, suggesting the increased telomere elongation in response to PARP acts through the ATM kinase pathway. Since different primers were used for STELA in this experiment the percentage of elongation differs compared to previous results (FIG. 3). Given this difference and the small magnitude of the change, this experiment has been repeated so that more definitive conclusions could be drawn. All of the results support the idea that PARP inhibition positively affects telomere length regulation by activating ATM kinase pathway.

Figure Legends

FIG. 8 shows inhibition of ATM blocks de novo telomere addition. (A) Analysis of PacBio® CCS reads (maximum of 300 shown for simplicity) is shown from samples pretreated with DSMO, 10 μM KU55933 or 5 nM siATM. X-axis indicates the length (bp) from the start of the telomere seed sequence. (B) The percentage of CCS reads with de novo telomere repeats are shown. n; number of independent biological replicates analyzed. (C) The sequences of PacBio® CCS reads from siATM treated sample boxed in (A) are shown.

Figure 9:
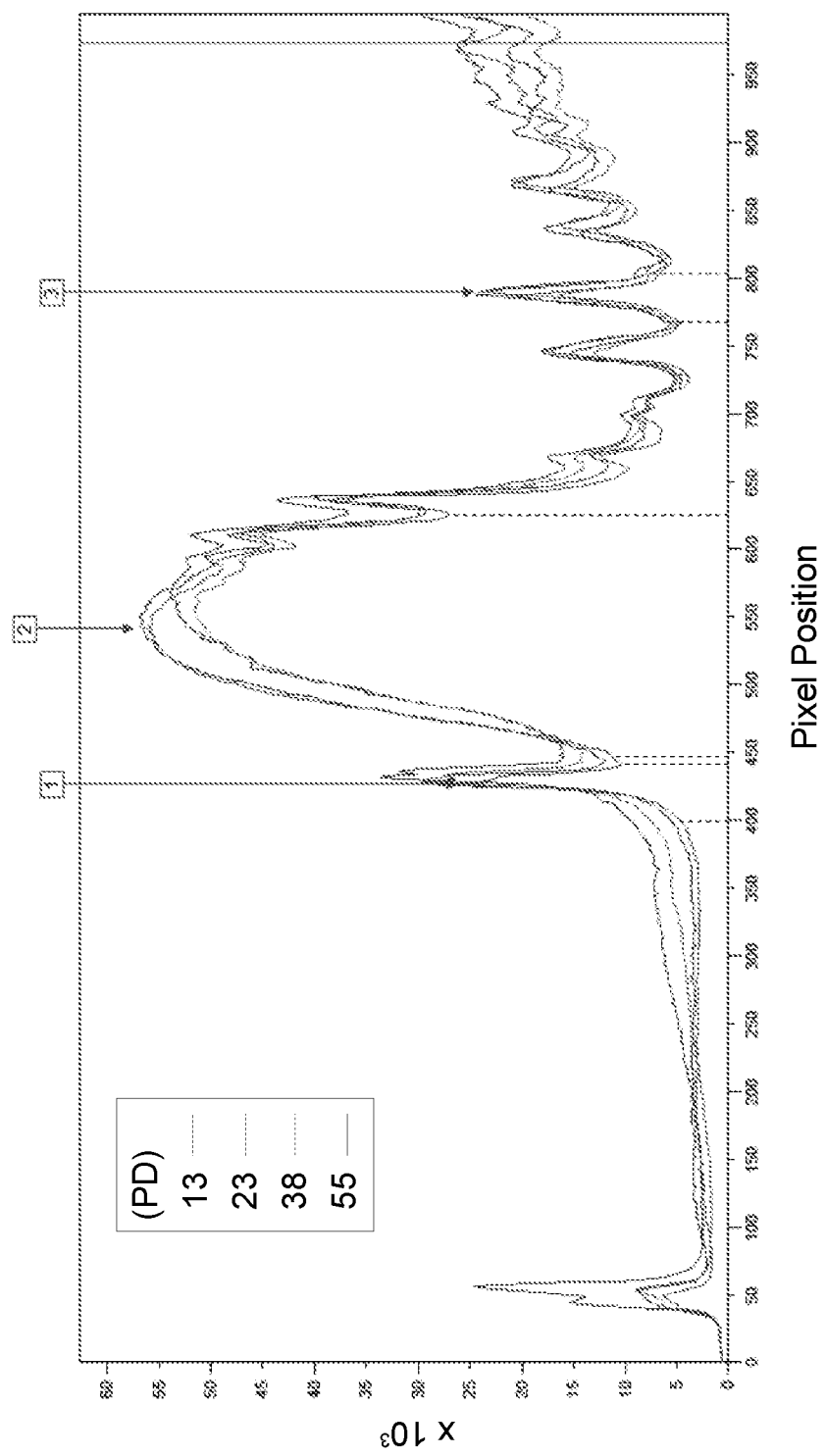
FIG. 9 is a graphical representation showing that telomere lengths shorten in the presence of ATM inhibitor KU55933.

FIG. 9 shows that telomere lengths shorten in the presence of ATM inhibitor KU55933. Telomere lengths of SL13 cells treated with 10 μM KU55933 were measured at different population doublings (PD) using genomic Southern blot analysis. Densitometry tracing of the Southern blot lanes by graphing pixel counts ($\times 10^3$) versus DNA migration distance (Pixel Position). Boxed numbers indicate the pixel positions corresponding to the blot in A.

Discussion

In this example, experiments are described using the ADDIT assay, that demonstrated the ATM kinase pathway is required for telomerase-mediated telomere addition. This conclusion was further substantiated using an alternative cell culture experiment approach; it was found that inhibition of ATM kinase activity prevents bulk telomere elongation by telomerase overexpression. In addition, blocking ATM kinase with KU55933 shortened telomeres in both mouse and human cells in long-term cell culture experiments. Furthermore, activation of ATM kinase pathway by using PARP inhibitor Olaparib significantly elongated telomeres, further supporting the role of ATM kinase promoting telomere elongation.

Conserved Pathways of Telomere Length Regulation

The mechanism of telomere length maintenance involves many interdependent regulatory pathways that act together to establish length homeostasis. This process involves the interaction of telomere binding proteins such as shelterin with telomerase to regulate elongation. In addition to dedicated telomere binding proteins, DNA damage proteins including MRN complex and Ku are conserved players in length maintenance from yeast to mammals. Protein modification also plays a key role in regulating telomere length. It was demonstrated that one of the key regulators of telomere length, the ATM kinase pathway, is also conserved from yeast to mammalian system. ATM is required for normal telomere maintenance in different yeast species including *S. pombe* and in these species ATM mediates the telomerase recruitment. The ATM homologue in *Arabidopsis* also plays a role in regulating telomere length by promoting elongation of short telomeres. *Drosophila* telomeres do not require telomerase for length maintenance, yet remarkably, the role of ATM is conserved in this species. These data suggest that even when telomerase was lost from this evolutionary branch of Diptera, the processes that regulate telomere length were still retained.

ATR May Compensate for Loss of ATM

The data, from both the ADDIT assay and Southern analysis, suggests the ATM kinase is required for telomere length maintenance. When ATM was inhibited by siRNA different results were seen in ADDIT assay and the longer term bulk culture experiment: telomere addition was completely blocked in ADDIT assay but not when cells were grown continuously in culture. This difference may be due to the transient siATM knockdown that does not sufficiently block ATM in longer-term culture conditions. Another possibility is that ATR kinase may compensate for ATM loss in the longer-term culture experiments. Previous studies in *S. cerevisiae* suggest ATR plays a minor, yet critical role in telomere maintenance. Cells lacking Tel1$^{ATM}$ are completely defective in telomere extension within the first few hours after the creation of short telomere. The bulk telomere lengths of Tel1$^{ATM}\Delta$ cells are short yet stable. Progressive telomere shortening is only seen when both tel1$^{ATM}$ and mec1$^{ATR}$ are deleted, suggesting Mec1$^{ATR}$ kinase may play some role in telomere elongation when Tel1$^{ATM}$ is missing. Similar to *S. cerevisiae*, the shortest telomere phenotype of *S. pombe* was seen in the Rad3$^{ATR}$/Tel1$^{ATM}$ double mutants (Naito et al., 1998). Interestingly, Rad3$^{ATR}$ mutant cells have much shorter telomere lengths compared to Tel1$^{ATM}$, indicating Rad3$^{ATR}$ may play a more critical role in telomere length regulation than does *S. pombe* Tel1$^{ATM}$.

Previous studies in mice indicated that ATM is not required for elongation of the shortest telomeres in an intergenerational cross. When the ATM$^{+/-}$ mice were crossed to ATM$^{+/+}$ mTR$^{-/-}$ G5 late generation mice with short telomeres, the F1 mice that resulted showed rescue of signal free ends in both ATM$^{+/+}$ mTR$^{+/-}$ and ATM$^{-/-}$ mTR$^{+/-}$ offspring, suggesting ATM is not essential for elongation of the shortest telomeres. This elongation, however, may be due to ATR compensating for the loss of ATM. The role of the ATR kinase in these pathways has not been examined as ATR null mice are not viable. In humans recent analysis indicated that Ataxia telangiectasia (AT) patients who have mutations in the ATM gene have shorter telomeres compared to their age-matched controls, but not as short as people who have telomerase mutations. This observation suggests ATR may also compensate for the loss of ATM function in telomere length maintenance in human. Dissecting the mechanism of telomere shortening in AT patients may have implications for individualized treatment. It is important to understand whether short telomeres can directly contribute to a more severe AT clinical phenotype and whether telomere lengthening could be a potential therapeutic target.

Possible Mechanisms of ATM Regulated Telomere Elongation

Previous findings in *S. cerevisiae* imply that the primary function of ATM in telomere maintenance is by modulating the access of telomerase to its substrate, telomere, rather than by altering the enzyme activity level of telomerase. The kinase activity of ATM is required for telomere maintenance as kinase dead mutant show short telomeres. While specific ATM substrates that affect telomere length have been characterized in *S. pombe*, the key substrates in *S. cerevisiae* are still not fully understood. In *S. pombe*, Tel1$^{ATM}$ and/or Rad3$^{ATR}$ phosphorylate a shelterin component Ccq1 that then interacts with telomerase subunit Est1 to mediate telomerase recruitment. In *S. cerevisiae*, while Tel1$^{ATM}$ can phosphorylate the single-strand telomere binding protein Cdc13, this phosphorylation apparently is not responsible for recruitment of Est1. While the precise functional homologues of Ccq1 and Est1 in mammalian cells are not fully established, likely due to sequence divergence and/or convergent evolution, shelterin components are still excellent candidates for ATM substrates in mammals given the conservation of length maintenance mechanisms across phyla. Previous studies in human cells suggest ATM phosphorylation of TRF1 can alter TRF1 association with telomeres, which can affect length regulation as well as end protection. Further, identification of ATM kinase target(s) will help us understand how ATM regulates telomerase recruitment and telomere elongation in mammalian cells.

PARP Regulation of ATM Regulated Telomere Length

PARP1 plays a critical role in DNA repair pathways, especially in base-excision repair, by binding to the single-strand break and forming poly (ADP-ribose) (PAR) polymer chains on itself and other proteins. PAR formation is thought to be important to protect DNA break and recruit DNA repair proteins to the site of DNA damage. In spite of these roles, PARP1 is not essential for cellular survival as PARP1 knockout mice are viable. Recently the PARP1/2 inhibitors have been developed for the treatment of cancer with the concept of using synthetic lethality to kill cancer cells. The idea is to treat certain cancers that have mutations in the DNA repair components, particularly BRCA1 or BRCA2, with PARP inhibitors and the additive effect of deficiency in two DNA damage pathways will cause cell death.

A previous study indicated that PARP inhibition would activate the ATM pathway. It was necessary to determine if PARP inhibitors would affect telomere length by activating the ATM kinase pathway. Olaparib was one of the first PARP1/2 specific inhibitors in the clinical trials. Treatment with Olaparib activated ATM and increased telomere length. It is very striking to observe such significant telomere elongation in cells treated with Olaparib, especially because Olaparib has become one of the first drugs approved by FDA to treat advanced ovarian cancers in December 2014 (2015). Although further validation is required, Olaparib may activate ATM kinase pathway resulting a positive effect on telomere length equilibrium. Given that Olaparib is used to treat cancer patients, it is crucial to fully characterize the secondary effects of Olaparib on telomere lengths.

The PARP enzyme family has 17 members, and the specificity of the PARP1/2 inhibitors may differ and have different consequences in mice and humans. For instance, in humans, tankyrase 1 and 2, members of PARP family, positively affect telomere length through the ADP ribosylation of TRF1. However, the interaction between tankyrases and TRF1 in human and mice differ significantly, resulting in different effects on telomere length. Previous study using in vitro assays indicated that several PARP1/2 inhibitors in clinical trials, including Olaparib, have strong specificities to PARP1-4 but less for others such as tankyrases. It will be important to verify whether these PARP inhibitors affect tankyrase activity in vivo to further understand the role of these drugs in telomere length regulation in humans.

ATM kinase pathway can also be activated by other ways such as oxidative stress without dsDNA breaks. Although chronic oxidative stress has been shown to enhance telomere shortening and cellular senescence in cultured cells, it will still be interesting to test whether very low level of oxidative stress, just enough to activate ATM kinase pathway, increases telomere lengths in mammalian cells. Ultimately finding a safe way to elongate telomeres, by discovery of a drug that activates the ATM kinase pathway, could benefit patients with telomere syndromes.

Material and Methods

Cell Culture and Treatments

Cell lines such as 293FT and HCT116 were grown in DMEM (Gibco) supplemented with 1% Penicillin/Streptomycin/Glutamine (PSG) and 10% heat inactivated FBS (Invitrogen). SL13 cells were grown in DMEM (Gibco) supplemented with 1% PSG and 10% Tet system approved FBS (Clontech, #631107). Final concentration of 2 µg/ml of doxycycline was added in the media to induce I-Sce1 expression. Typically cells were collected post 48 hours of doxycycline treatment. To inhibit ATM kinase activity, the ATM specific inhibitor KU55933 (R&D Systems, #3544) was added at the final concentration of 10 µM. To activate ATM kinase pathway, PARP1/2 inhibitor Olaparib (Selleckchem.com, #S1060) was used at the final concentration of 1 µM, 3 µM or 5 µM.

siRNA-Mediated Knockdown of ATM and ATR

ON-TARGET™ siRNA SMART pools from GE Healthcare were used: mouse ATM (11920), mouse ATR (245000). SL13 cells were subject to transfection using Pepmute™ protocol (SignaGen Laboratories, #SL100566). The final concentrations of siRNAs were 5 nM, 10 nM or 100 nM for each transfection. The efficiency of knockdown was assessed by immunoblotting.

Western Blot Analysis and Antibodies

To detect phospho-proteins, 1× lysis buffer made of final concentration of 1× RIPA (Cell Signaling, #98016S), 1× protease inhibitor cocktail, 1× PhosSTOP™ (Roche, #4906845001) was added directly to cells on the dish after washing with cold 1× PBS. Protein concentration was measured with a BCA protein assay kit (Thermo, #23227). Typically 10 µg of protein from each sample was applied to SDS-PAGE gels, 4-15% Mini-PROTEAN TGX™ gels (Biorad, #456-1084), and transferred to nitrocellulose membranes in transfer buffer. After blocking with the Odyssey™ blocking buffer (LI-COR, #927-40000) for 1 hour at RT, membranes were incubated at 4° C. overnight with the following primary antibodies multiplexed: anti-phospho-Kap1 (Bethyl Lab, #A300-767A); anti-ATM (Novusbio, #NB100-220); anti-phospho-CHK1 (Cell Signaling, #2348S); anti-Actin (Santa Cruz, #sc-1616). The following day, blots are washed with 1× PBS-T 3× 15 minutes, and then incubated with secondary antibodies conjugated to near-infrared dyes (IRDye® 680 anti-goat, 800 anti-rabbit, 800 anti-mouse, LI-COR). Blots were scanned on a two-channel near-infrared Odyssey scanner (LI-COR). Band intensities were quantified using the Odyssey™ software (LI-COR) and normalized to Actin levels. Certain antibodies were not multiplexed, instead after 4° C. overnight incubation with the primary antibody, blot was washed and incubated with the following HRP-conjugated secondary antibodies: anti-mouse IgG HRP-linker antibody (Cell Signaling, #7076) and anti-goat IgG HRP-conjugate antibody (Biorad, #172-1034). The blot was scanned using the ImageQuant LAS 4000™ imager (GE Healthcare). To re-probe the same blot with a loading control antibody, the blot was stripped with a stripping buffer (Thermo, #46430) and processed as described above.

Telomere Southern Analysis

To measure telomere lengths by Southern blot, genomic DNA was extracted from cell pellets collected at different population doublings using the Puregene Core Kit A™ (Qiagen). Equal amounts of genomic DNA were digested overnight with MseI restriction enzyme (NEB) and loaded on a 0.7% TAE agarose gel. Samples were run at 100V for roughly 6 hours. Following denaturation (0.5 M NaOH/1.5 M NaCl) and neutralization (1.5 M NaCl/0.5 M Tris-HCL pH 7.4), the DNA was transferred in 20× SSC to a Nylon Membrane (Amersham Hybond N+) by weighting method overnight and cross-linked with UV Stratalinker (Stratagene). Pre-hybridization was done at 65° C. in Church's buffer for 2 hours. A radioactive telomere probe was made by random-prime labeling using Prime-It II (Stratagene) with a slight modification. Briefly, 25 ng of a 500 bp telomeric 5'-TTAGGG containing probe acquired from EcoRI digestion of JHU821 or 1 KB Plus DNA ladder (Invitrogen) was labeled using 33 µM of dATP, dTTP, dGTP and 50 µCi of α-32P dCTP (3000 Ci/mmol). Unincorporated nucleotides were removed using a G50 column (GE Healthcare). Labeled probe was counted and $10^6$ counts/ml (telomere probe) or $10^4$ counts/ml (ladder) was denatured at 100° C. for 5 minutes and added to the pre-hybridization solution and hybridized overnight at 65° C. Membranes were washed 3× 15 minutes each in 6× SSC and 1% SDS at 65° C., and 3× 15 minutes each in 1× SSC and 1% SDS at 65° C. and exposed to a phosphorimager screen and detected on a Fuji phosphorimager. Image processing software, ImageQuant™ 1D v8.1 (GE Healthcare Life Sciences), was used to generate densitometry of Southern blot lanes by graphing pixel counts versus DNA migration distance.

Lentivirus Transduction

SL13 cells were seeded in complete medium with either DMSO or KU55933, or pre-transfected with siATM (siRNA transfection described in 4.4.2) in 6-well plates. The following day, polybrene-treated cells (8 µg/ml, Sigma) were infected with SVA (mTR/mTERT double construct) lentivirus, MOI≤1, and incubated overnight at 37° C., 5% $CO_2$. The following morning, the medium was changed to eliminate the polybrene and refreshed with complete medium either with DMSO or KU55933. After 2 days of transduction, aliquots of cells were collected for Southern analysis and the rest of cells were re-plated in the presence of DMSO, KU55933 or transfected with siATM.

Modified Single Telomere Length Analysis (STELA) for chr4

To multiplex samples treated with different conditions for PacBio® sequencing, the STELA PCR for chr4 described in 2.4.9 was performed with slight modification. Briefly, the 20-nt unique sequence of telorette was randomized to make several different sets of unique telorette linkers. The different sets of telorette have corresponding teltail primers that recognize the unique sequence. In some experiments, degenerated forward HYG primers and reverse teltail primers were used.

PacBio® Sequence Analysis

PacBio® sequence reads were analyzed as described in Example 1.

TABLE 2

Oligonucleotide list

Modified STELA for chr4

| | |
|---|---|
| Telorette 1 | TGCTCCGTGCATCTGGCATCCCCTAAC (SEQ ID NO: 90) |
| Telorette 2 | TGCTCCGTGCATCTGGCATCTAACCCT (SEQ ID NO: 91) |
| Telorette 3 | TGCTCCGTGCATCTGGCATCCCTAACC (SEQ ID NO: 92) |
| Telorette 4 | TGCTCCGTGCATCTGGCATCCTAACCC (SEQ ID NO: 93) |
| Telorette 5 | TGCTCCGTGCATCTGGCATCAACCCTA (SEQ ID NO: 94) |
| Telorette 6 | TGCTCCGTGCATCTGGCATCACCCTAA (SEQ ID NO: 95) |
| Iscerette | TGCTCCGTGCATCTGGCATCTTAT (SEQ ID NO: 96) |
| HYG-specific F1 | CTGAACTCACCGCGACGTCTGT (SEQ ID NO: 97) |
| HYG-specific F2 | AGGAGGGCGTGGATATGTCCTGCGG (SEQ ID NO: 98) |

TABLE 2-continued

Oligonucleotide list

| Name | Sequence |
|---|---|
| Teltail | TGCTCCGTGCATCTGGCATC (SEQ ID NO: 99) |
| Teltail B | TGCTCGCGTACCTGTGCATC (SEQ ID NO: 100) |
| Telorette B 1 | TGCTCGCGTACCTGTGCATCCCCTAAC (SEQ ID NO: 101) |
| Telorette B 2 | TGCTCGCGTACCTGTGCATCTAACCCT (SEQ ID NO: 102) |
| Telorette B 3 | TGCTCGCGTACCTGTGCATCCCTAACC (SEQ ID NO: 103) |
| Telorette B 4 | TGCTCGCGTACCTGTGCATCCTAACCC (SEQ ID NO: 104) |
| Telorette B 5 | TGCTCGCGTACCTGTGCATCAACCCTA (SEQ ID NO: 105) |
| Telorette B 6 | TGCTCGCGTACCTGTGCATCACCCTAA (SEQ ID NO: 106) |
| Teltail C | TGCGCACTGCATGTGTCCTC (SEQ ID NO: 107) |
| Telorette C 1 | TGCGCACTGCATGTGTCCTCCCCTAAC (SEQ ID NO: 108) |
| Telorette C 2 | TGCGCACTGCATGTGTCCTCTAACCCT (SEQ ID NO: 109) |
| Telorette C 3 | TGCGCACTGCATGTGTCCTCCCTAACC (SEQ ID NO: 110) |
| Telorette C 4 | TGCGCACTGCATGTGTCCTCCTAACCC (SEQ ID NO: 111) |
| Telorette C 5 | TGCGCACTGCATGTGTCCTCAACCCTA (SEQ ID NO: 112) |
| Telorette C 6 | TGCGCACTGCATGTGTCCTCACCCTAA (SEQ ID NO: 113) |
| Teltail D | TGCGTGTCCCTGCATGCATC (SEQ ID NO: 114) |
| Telorette D 1 | TGCGTGTCCCTGCATGCATCCCCTAAC (SEQ ID NO: 115) |
| Telorette D 2 | TGCGTGTCCCTGCATGCATCTAACCCT (SEQ ID NO: 116) |
| Telorette D 3 | TGCGTGTCCCTGCATGCATCCCTAACC (SEQ ID NO: 117) |
| Telorette D 4 | TGCGTGTCCCTGCATGCATCCTAACCC (SEQ ID NO: 118) |
| Telorette D 5 | TGCGTGTCCCTGCATGCATCAACCCTA (SEQ ID NO: 119) |
| Telorette D 6 | TGCGTGTCCCTGCATGCATCACCCTAA (SEQ ID NO: 120) |
| Teltail E | TGCCTGCATGTGTCCGCATC (SEQ ID NO: 121) |
| Telorette E 1 | TGCCTGCATGTGTCCGCATCCCCTAAC (SEQ ID NO: 122) |
| Telorette E 2 | TGCCTGCATGTGTCCGCATCTAACCCT (SEQ ID NO: 123) |
| Telorette E 3 | TGCCTGCATGTGTCCGCATCCCTAACC (SEQ ID NO: 124) |
| Telorette E 4 | TGCCTGCATGTGTCCGCATCCTAACCC (SEQ ID NO: 125) |
| Telorette E 5 | TGCCTGCATGTGTCCGCATCAACCCTA (SEQ ID NO: 126) |
| Telorette E 6 | TGCCTGCATGTGTCCGCATCACCCTAA (SEQ ID NO: 127) |
| Teltail_F | TGCTCCGCACTGCATGTGTC (SEQ ID NO: 128) |
| Telorette_F 1 | TGCTCCGCACTGCATGTGTCCCCTAAC (SEQ ID NO: 129) |
| Telorette_F 2 | TGCTCCGCACTGCATGTGTCTAACCCT (SEQ ID NO: 130) |
| Telorette_F 3 | TGCTCCGCACTGCATGTGTCCCTAACC (SEQ ID NO: 131) |
| Telorette_F 4 | TGCTCCGCACTGCATGTGTCCTAACCC (SEQ ID NO: 132) |
| Telorette_F 5 | TGCTCCGCACTGCATGTGTCAACCCTA (SEQ ID NO: 133) |
| Telorette_F 6 | TGCTCCGCACTGCATGTGTCACCCTAA (SEQ ID NO: 134) |
| N-Teltail | NNNNTGCTCCGTGCATCTGGCATC (SEQ ID NO: 135) |
| N-Teltail B | NNNNTGCTCGCGTACCTGTGCATC (SEQ ID NO: 136) |
| N-Teltail C | NNNNTGCGCACTGCATGTGTCCTC (SEQ ID NO: 137) |
| N-Teltail D | NNNNTGCGTGTCCCTGCATGCATC (SEQ ID NO: 138) |
| N-Teltail E | NNNNTGCCTGCATGTGTCCGCATC (SEQ ID NO: 139) |
| N-Teltail F | NNNNTGCTCCGCACTGCATGTGTC (SEQ ID NO: 140) |
| N-HYG FOR1 | NNNNCTGAACTCACCGCGACGTCTGT (SEQ ID NO: 141) |
| N-HYG_FOR3 | NNNNAGGAGGGCGTGGATATGTCCTGCGG (SEQ ID NO: 142) |

EXAMPLE 3

Role of Cyclin-Dependent Kinases in Telomere Length Regulation

Telomeres are specialized structures at the ends of the linear chromosome that allow cells to distinguish the natural ends from double-strand DNA break. Failure to maintain telomere structure can result in chromosome fusions and genomic instability. Telomere structure, and the enzyme telomerase that is responsible for synthesizing telomeric repeats, are highly conserved. Telomere DNA consists of a short tandem repeats of a short G-rich sequence with a stretch of 3' overhang. This G-rich 3' overhang structure of telomeres is conserved throughout eukaryotes, including ciliates, fungi and mammals. The proteins that interact with the 3' single-strand overhang and those that bind the double-strand telomeric repeats have important roles in maintaining telomere lengths as they are involved in protecting telomere ends and modulating telomerase access to telomeres.

Most of the key players and requirements for telomere length regulation have been investigated in the model organism S.cerevisiae, including cyclin-dependent kinase (Cdk). Cdks are serine/theornine kinases responsible for various cellular processes such as cell cycle progression and transcription. In both S.cerevisiae and S.pombe, a single Cdk, Cdk1, is responsible for regulating cell cycle transitions. In addition to its critical role in cell cycle regulation, a previous study from our lab showed that Cdk1 is required for telomere elongation by regulating the generation of the 3' overhang. In higher eukaryotes, there are a growing number of Cdk family members identified. Functional characterization of these Cdks elucidated specific roles in different cellular processes such as cell cycle regulation, transcription and others, but the role in telomere length regulation is not well elucidated.

This example illustrates that telomerase-mediated telomere addition is regulated in a cell-cycle dependent manner in mammalian cells, and that mammalian Cdks, including Cdk1, are required for telomere elongation in vivo.

Results

De Novo Telomere Addition Occurs in G2/M Phase

To better understand how mammalian telomere length is regulated, the short-term ADDIT assay was used to visualize telomere addition in vivo. Briefly, an inducible I-Sce1 site is used to create a double-strand DNA break adjacent to a stretch of telomere 'seed' sequence near the end of a single chromosome (chr4). Given that telomere elongation in cycling cells was observed, whether telomere addition could be visualized in cells arrested at distinct cell cycle phases was tested to determine if telomere addition is cell cycle regulated in a similar manner to yeast. SL13 cells were arrested in G2/M phase using colcemid, a drug that depolymerizes microtubules limiting microtubule formation during M phase, or in G1/early S phase by thymidine block. Cells accumulated at the expected cell phases using PI staining and flow cytometry analysis (FIG. 10A) and then induced doxycycline to expose the telomere seed sequence. The 'smear' representative of de novo telomere addition is not robustly detected by Southern blot analysis. However even less 'smear' from cells arrested in G1 phase was observed compared to controls cells and cells held in G2/M phase suggesting that telomere elongation may be dependent on cell cycle. To better visualize the de novo telomere addition, STELA PCR products of SL13 cells pretreated with colcemid or DMSO were sequenced. Consistent with the results from yeast, cells held in G2/M phase had significant percentage of PacBio® reads with de novo telomere addition (FIG. 10C). No significant difference of de novo elongation was observed between cycling cells or cells arrested in G2/M phase. To ensure I-Sce1 induction is consistent across different cell cycle phases, I-Sce1 expression was measured in cells arrested at different phases and confirmed no significant difference (FIG. 10B). These results suggest that the requirements for telomere elongation are present in G2/M phase in mammalian cells similar to yeast.

Telomere Addition is Dependent on Cyclin-Dependent Kinases

Cdk1 positively regulates telomere elongation in S.cerevisiae. To examine whether Cdk activity plays a similar role in telomere elongation in mammalian cells, several methods were tested to inhibit Cdks and performed the short-term ADDIT assay. Cells were treated either with or without flavopiridol, which inhibits several members of the Cdk family, including Cdk1, 2, 4, 6, 7. Southern blot analysis of STELA PCR products from flavopiridol-treated sample suggested minimal elongation beyond the chr4 I-Sce1-induced cut base line. PacBio® sequences from the STELA products indeed showed treatment with flavopiridol significantly reduced de novo telomere addition (FIG. 11), from 24% to less than 2%, suggesting Cdk activities are required for telomere elongation.

Cdk1 is Required for De Novo Telomere Addition

To determine which of the several Cdks in mammalian cells, is responsible for regulating telomere length, the effect of knocking down Cdk1 was first tested since the Cdk1 homologue in yeast has been shown to be required for telomere elongation. Cells were treated with siRNA against Cdk1 and confirmed more than 50% knockdown by measuring the phosphorylation level of Cdk1-Y15. ADDIT assay was performed in cells treated with or without siCdk1. PacBio® sequence analysis of the STELA PCR products indicated de novo telomere addition was completely blocked in cells with Cdk1 knockdown (FIGS. 11A and 11B). These observations suggest the requirement of Cdk1 in telomere elongation is conserved from yeast to mammalian cells.

Figure Legends

FIG. 10 shows that de novo telomere addition occurs in G2/M phase. (A) SL cells treated with either DMSO, 200 ng/ml colcemid or 2.5 mM thymidine for 24 hrs were analyzed for cell cycle profile by propidium iodide staining and flow cytometry. The numbers indicate the percentage of cells in each cell cycle phase. (B) Relative expression levels of HA-tagged I-Sce1 normalized to HPRT measured by quantitative RT-PCR. Error bars indicate the standard error of mean (SEM) from triplicates of SL13 cells treated with 200 ng/ml colcemid, 2.5 mM thymidine or DMSO for 48 hrs. (C) Analysis of PacBio CCS reads (maximum of 300 shown for simplicity) of STELA PCR products made from cells treated with either DMSO or 200 ng/ml colcemid for 48 hrs. X-axis indicates the length (bp) from the start of the telomere seed sequence. The percentage of PACBIO® CCS reads with de novo telomere repeats are calculated from each sample by using the following formula: $100\% \times \{$(number of CCS reads with telomere repeats added beyond the I-Sce1 site)/(number of total CCS reads)$\}$.

Figure 11:
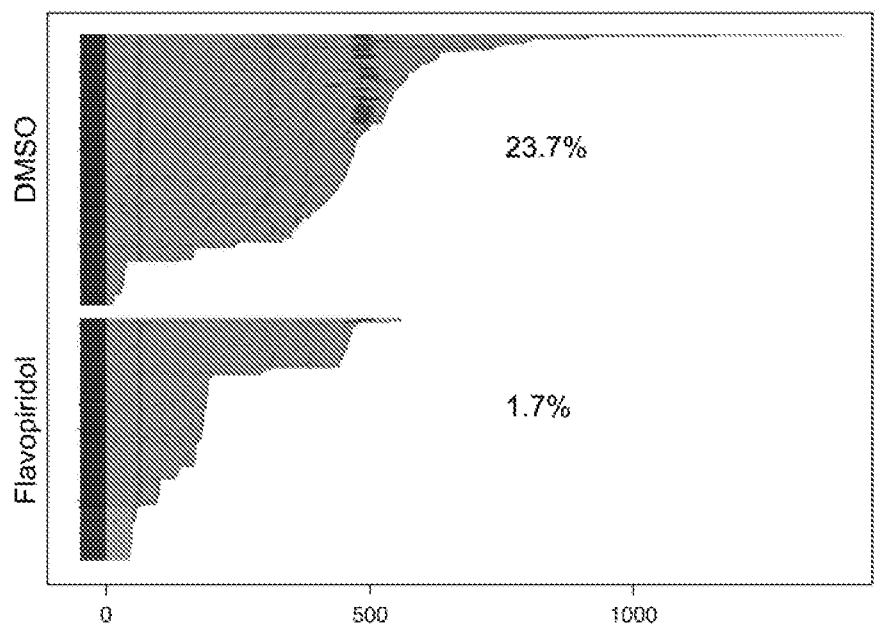
FIG. 11 is a graphical representation showing that inhibition of Cdks prevents de novo telomere addition.

FIG. 11 shows that inhibition of Cdks prevents de novo telomere addition. Cells were treated with final concentration 400 nM of flavopiridol or DMSO together with or without 200 ng/ml colcemid, and exposed to doxycycline for 48 hrs. STELA PCR products made with a F2 primer were analyzed by Southern hybridization using HYG probe. Analysis of PACBIO® CCS reads (maximum of 200 reads for simplicity) from samples treated with either 400 nM flavopiridol or DMSO for 48 hrs. X-axis indicates the length (bp) from the start of the telomere seed sequence. The percentages of reads with de novo telomere addition are shown.

Figure 12A:
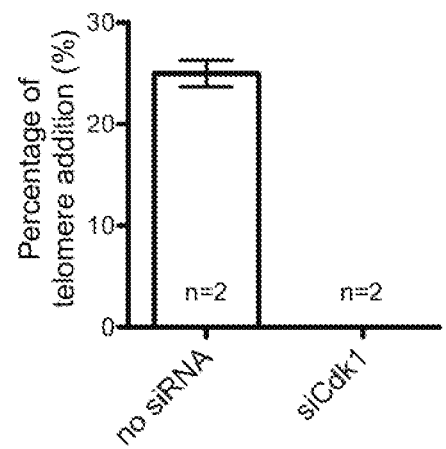
FIGS. 12A and 12B are graphical representations showing that Cdk1 is required for de novo telomere addition.
Figure 12B:
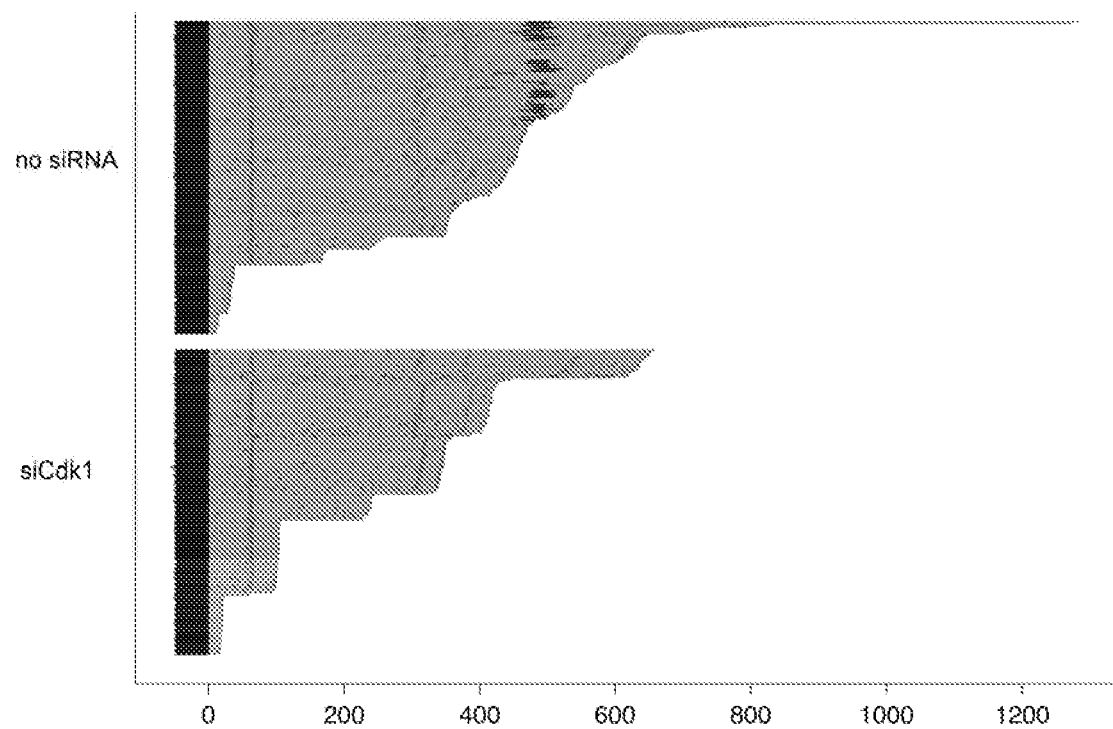

FIG. 12 shows Cdk1 is required for de novo telomere addition. Phosphorylation levels of Cdk1 were analyzed by immunobloting cells treated with 10.mu.M R03306 or different final concentration of siCdk1, 5 nM, 10 nM or 100 nM. Numbers at bottom of western indicate the relative expression levels of phosphorylated Cdk1-T15 normalized to Actin. (A) Percentages of CCS reads with de novo telomere addition from samples treated with either DMSO or final concentration of 5 nM siCdk1 for 48 hrs. n; number of independent biological replicates analyzed. (B) Analysis of PACBIO® CCS reads (maximum of 200 reads for simplicity) from (A) shown. X-axis indicates the length (bp) from the start of the telomere seed sequence.

Discussion

In the experiments presented in this example, the ADDIT assay was used to visualize telomerase-mediated de novo telomere addition occurred in cycling cells but also in cells held in G2/M phase. On the other hand, although further validation is required, Southern blot analysis suggested cells arrested in G1-phase has inefficient telomere elongation. In addition, it was shown that mammalian Cdks, especially Cdk1, are required for telomere addition. Since Cdk1 is an essential gene required for early embryonic development, it would not be possible to address the role of this kinase with the conventional method of measuring bulk telomere length changes for over 2 months; however, the very brief time required for ADDIT assay overcame this issue and allowed us to examine the critical role of Cdk1 in telomere addition.

Telomere Elongation is Cell Cycle Regulated

Previous work using the de novo telomere addition assay in S.cerevisiae demonstrated that when cells are arrested in G1 phase using the mating pheromone α-factor, the telomere seed is not elongated whereas the end was efficiently elongated in vivo in cells arrested in M phase by treatment with the microtubule depolymerizing drug nocodazole. Telomerase activity was present in extracts made from all cell cycle phases; however, telomere addition was restricted to late S/G2 phase. Consistent with the results from yeast, efficient telomere addition was observed in SL13 cells held in G2/M phase but not in G1, suggesting cell cycle-coordinated telomere elongation is a conserved phenomenon. These observations suggest that essential component(s) mediating telomere elongation maybe absent or inactivated in certain cell cycle phases. The precise timing and coordination of telomerase recruitment to telomeres are regulated by ATM kinase (as discussed herein) and other mechanisms that have not been fully elucidated.

Cdks are excellent candidates for regulating cell cycle-dependent telomere elongation. The data indicate Cdk1 has an essential role in telomere elongation. A previous study reported that TRF2 (telomeric-repeat-binding factor 2) is a Cdk1 and Cdk2 substrate by high throughput in vitro kinase screening. Although further validation is necessary, Cdk1 and/or Cdk2 may regulate telomere length by interacting and phosphorylating TRF2 in vivo. It is possible other Cdks also regulate telomere length homeostasis.

Previous studies suggest DNA polymerase and primase, which are involved in telomere lagging strand synthesis, are also required for functional telomere elongation. It will be interesting to further dissect the telomere replication machinery to identify cell cycle-dependent components required for mammalian telomere elongation using the ADDIT assay.

The Essential Role of Cdk1 in Telomere Addition

Previous studies have shown that many of the key regulators required for telomere length maintenance are identical between the natural telomeres and de novo telomere ends. The yeast Cdk1 activity is also required to generate the 3' G-rich overhang, which is important for telomere length maintenance, at both de novo telomere ends as well as the natural telomeres. It is possible that Cdk1 activates a nuclease(s) that is involved in single-strand resection, such as Mre11 that is involved in resection at double-strand DNA break sites. In yeast, Cdk1 phosphorylates the nuclease Dna2, which is involved in generating the 3' overhang at telomeres. It will be interesting to find whether mammalian Cdk1 is also responsible for generating the 3' overhang by activating a nuclease(s) responsible for 5' strand resection.

In addition, Cdk1 appears to be involved in regulating telomerase recruitment. In S.cerevisiae, phosphorylation of the single-strand DNA binding protein Cdc13 (T308) by Cdk1 promotes the interaction between Cdc13 and one of the telomerase components, Est1, resulting in telomerase recruitment and telomere elongation. A recent study showed S.cerevisiae Cdk1 also phosphorylates Stn1, one of the other components of CST complex (Cdc13-STN1-TEN1), which stabilizes the complex at telomeres. The CST complex is conserved in higher eukaryotes with an exception that mammalian CST complex consists CTC1 instead of Cdc13. Recent studies purpose human CST (CTC1-STN1-TEN1) complex inhibits telomere elongation by competing with POT1-TPP1 and promotes telomere replication at C-strand by stimulating DNA polymerase α-primase. The results from ADDIT assay demonstrated that Cdk1 activity is also required for de novo telomere addition in mammalian cells (FIGS. 12B and 12C), indicating the conserved role of Cdk1 in telomere length regulation in higher eukaryotes. A previous study showed phosphorylation of TPP1 (S111) affects telomerase interaction in a cell cycle dependent manner and is lost in the presence of Cdk inhibitor. It will be interesting to elucidate how mammalian Cdk1 regulates telomere elongation, and further test whether Cdk1-mediated phosphorylation(s) of CST complex and/or shelterin complex components, such as TPP1, exist.

Materials and Methods

Cell Culture and Treatments

SL13 cells were grown in DMEM (Gibco) supplemented with 1% Penicillin/Streptomycin/Glutamine and 10% Tet system approved FBS (Clontech, #631107). Final concentration of 2 μg/ml of doxycycline was added in the media to induce I-Sce1 expression. Typically cells were collected post 48 hours of doxycycline treatment. To arrest cells in different cell cycle phases, cells were treated with either final concentration of 200 ng/ml colcemid (Gibco KaryoMAX Colcemid Solution, #15212-012) or 2.5 mM Thymidine (Sigma, #T-1895).

Cell Cycle Profile Analysis

Cell cycle phase was accessed by DNA content using propidium iodide (PI) staining and flow cytometry analysis. Briefly, cell pellets were washed with 1× PBS at 500× g for 5 minutes and resuspended in 500 μl of 1× PBS. 4.5 ml of ice cold 70% ethanol was added drop by drop, and incubated overnight at 4° C. Samples were washed with 5 ml 1× PBS and incubated with 500 μl of PI-Triton resuspension buffer at room temperature for ≥30 minutes protected from light. PI-Triton resuspension buffer was made of 0.1% Triton™ X-100, 200 μg/ml RNase A, 20 μg/ml PI (Invitrogen, #P3566) in 1× PBS. PI-stained samples were transferred to strainer tubes (BD Falcon) and run on FACSCalibur™ flow cytometry (BD Biosciences). Cell cycle profiles were analyzed utilizing the Dean-Jet-Fox™ model in FlowJo™ software (FlowJo™).

Quantitative RT-PCR

To measure HA-tagged I-Sce1 expression levels, quantitative RT-PCR was performed as described in 2.4.5. Primers used are the following: HA-ISce1-FOR, 5'-TCCTGAC-TATGCGGGTATGA-3' (SEQ ID NO: 143); ISce1-REV2, 5'-CCTTCATCACGAGAACGGAT-3' (SEQ ID NO: 144); HPRT_F, 5'-TGATCAGTCAACGGGGGACA-3' (SEQ ID NO: 145); HPRT_R, 5'-TTCGAGAGGTCCTTTTCACCA-3' (SEQ ID NO: 146).

Southern Blot Analysis

To examine the in vivo chr4 cleavage and de novo telomere addition, genomic DNA extracted from SL13 cells arrested at different cell phases and treated with doxycycline for various time points were digested with NcoI restriction enzyme (NEB) and further analyzed by Southern blot as described previously in Example 1 with a random primed α-32P-labeled HYG probe.

siRNA-Mediated Knockdown of Cdk1

ON-TARGET™ siRNA SMART pools from GE Healthcare were used: mouse Cdk1 (L-058633-00-0005). SL13 cells were subject to siRNA transfection using Pepmute™ protocol (SignaGen Laboratories, #SL100566) at a final concentration of 5 nM, 10 nM or 100 nM. The efficiency of knockdown was assessed by immunoblotting.

Western Blot Analysis and Antibodies

Cell lysates were made and processed as described in 3.4.3. Membranes were incubated at 4° C. overnight with primary antibodies: anti-phospho-Cdk1 (Cell Signaling, #9111) and anti-Actin (Santa Cruz, #sc-1616). After incubation with secondary antibodies conjugated to near-infrared dyes (IRDye® 680 anti-goat, 800 anti-rabbit, LI-COR), blots were scanned on a two-channel near-infrared Odyssey™ scanner (LI-COR).

Modified Single Telomere Length Analysis (STELA) for chr4

The original STELA protocol used for human cells was modified to measure the de novo telomere addition on chr4 in SL13 cells as described in previously.

PacBio® Sequence Analysis

PacBio® sequence reads were analyzed as described in previously.

Although the invention has been described with reference to the above example, it will be understood that modifications and variations are encompassed within the spirit and scope of the invention. Accordingly, the invention is limited only by the following claims.

What is claimed is:

1. A method of identifying a regulator of telomere length comprising: a) culturing a murine cell in the presence and absence of an agent that modulates expression of a selected gene or pathway in the cell, wherein the murine cell comprises (i) a modified chromosome containing an internal telomere seed sequence and an endonuclease cleavage site downstream of the telomere seed sequence, wherein the cell conditionally expresses an endonuclease that cleaves and exposes the telomere seed sequence, and (ii) a recombinant nucleic acid sequence encoding a telomerase; and b) measuring de novo telomere addition to the seed sequence in the presence and absence of the agent, wherein addition of telomere sequence in the presence of the agent, but not in the absence of the agent, is indicative of identification of the agent as being a regulator of telomere length, thereby identifying a regulator of telomere length.

2. The method of claim 1, wherein the murine cell further comprises a recombinant nucleic acid sequence encoding a recombinase.

3. The method of claim 2, wherein the recombinant nucleic acid sequence encoding telomerase further comprises a recombinase target sequence allowing excision of the nucleic acid sequence encoding telomerase.

4. The method of claim 1, wherein the murine cell further comprises a recombinant nucleic acid sequence encoding an endonuclease specific for the endonuclease cleavage site.

5. The method of claim 4, wherein the endonuclease is I-SceI.

6. The method of claim 4, wherein the recombinant nucleic acid sequence encoding an endonuclease is operably linked to an inducible promoter.

7. The method of claim 6, wherein the promoter is inducible by a tetracycline antibiotic.

8. The method of claim 7, wherein the tetracycline antibiotic is doxycycline.

9. The method of claim 1, wherein the measuring comprises polymerase chain reaction (PCR).

* * * * *